US011364219B2

(12) United States Patent
Chamaillard

(10) Patent No.: US 11,364,219 B2
(45) Date of Patent: Jun. 21, 2022

(54) METHODS AND PHARMACEUTICAL COMPOSITIONS FOR TREATING MICROBIOME DYSREGULATIONS ASSOCIATED WITH CIRCADIAN CLOCK DISRUPTION

(71) Applicants: INSERM (INSTITUT NATIONAL DE LA SANTÉ ET DE LA RECHERCHE MÉDICALE), Paris (FR); UNIVERSITE DE LILLE, Lille (FR); INSTITUT PASTEUR DE LILLE, Lille (FR); CENTRE NATIONAL DE LA RECHERCHE SCIENTIFIQUE—CNRS-, Paris (FR)

(72) Inventor: Mathias Chamaillard, Lille (FR)

(73) Assignees: INSERM (INSTITUT NATION DE LA SANTÉ ET DE LA RECHERCHE MÉDICALE), Paris (FR); UNIVERSITE DE LILLE, Lille (FR); INSTITUT PASTEUR DE LILLE, Lille (FR); CENTRE NATIONAL DE LA RECHERCHE SCIENTIFIQUE—CRNS—, Paris (FR)

( * ) Notice: Subject to any disclaimer, the term of this patent is extended or adjusted under 35 U.S.C. 154(b) by 0 days.

(21) Appl. No.: 16/303,249

(22) PCT Filed: May 19, 2017

(86) PCT No.: PCT/EP2017/062163
§ 371 (c)(1),
(2) Date: Nov. 20, 2018

(87) PCT Pub. No.: WO2017/198847
PCT Pub. Date: Nov. 23, 2017

(65) Prior Publication Data
US 2020/0390740 A1    Dec. 17, 2020

(30) Foreign Application Priority Data
May 20, 2016 (EP) .................................. 16305585

(51) Int. Cl.
| A61K 45/06 | (2006.01) |
| C07D 487/04 | (2006.01) |
| A61K 31/4985 | (2006.01) |
| A61K 31/5377 | (2006.01) |
| A61K 31/353 | (2006.01) |
| A61P 1/00 | (2006.01) |
| A61K 31/277 | (2006.01) |

(52) U.S. Cl.
CPC .......... *A61K 31/353* (2013.01); *A61K 31/277* (2013.01); *A61P 1/00* (2018.01)

(58) Field of Classification Search
CPC ........ A61K 31/353; A61K 31/273; A61P 1/00
See application file for complete search history.

(56) References Cited

U.S. PATENT DOCUMENTS

2012/0328593 A1* 12/2012 Huang ...................... A61P 1/04
424/94.4

FOREIGN PATENT DOCUMENTS

| JP | 2008 266319 A | 11/2008 |
| WO | 2010/121225 A2 | 10/2010 |

OTHER PUBLICATIONS

Voigt et al. PLOS ONE (2014);9(5); 1-17).*
Rosselot et al. (Curr Opin Gastroenterol. Jan. 2016 ; 32(1): 7-11).*
Thaiss Christoph A et al., "Transkingdom control of Bicrobiota Diurnal Oscillations Promotes Metabolic Homeostasis", Cell, Cell Press, US, vol. 159, No. 3, Oct. 16, 2014, pp. 514-529.
Data Biosis [Online] Biosciences Information Service, Philadelphia, PA, US, 2003, Parhar Kuljit et al., Potential Roll of Protein Kinase CK2 in IL-1BETA-Induced Epithelial Cell Function.
Teresa Vezza et al., "Flavonoids in Inflammatory Bowel Disease: A Review", Nutrients, vol. 8, No. 4, Apr. 9, 2016, p. 211.
Mukherji Atish et al. , "Homeostasis in Intestinal Epithelium Is Orchestrated by the Circadian Clock and Microbiota Cues Transduced by TLRs", Cell, Cell Press, US, vol. 153, No. 4, May 9, 2013, pp. 812-827.
Thaiss C A et al., "A day in the life of the meta-organism: Diurnal rhythms of the intestinal microbiome and its host", Gut Microbes, Landes Bioscience, United States, vol. 6, No. 2, Apr. 22, 2015, pp. 137-142.

* cited by examiner

*Primary Examiner* — Shirley V Gembeh
(74) *Attorney, Agent, or Firm* — WCF IP

(57) ABSTRACT

The present invention relates to the treatment of microbiome dysregulations. Said dysregulations may subsequently contribute to the development of several chronic diseases. Thus characterization of new post-biotic compounds inducing beneficial changes on host-microbiota interactions may be highly desirable. The inventors showed that Nlrp6 diurnally coordinates cyclical adaptation of the gut microbiota diversity to epithelial plasticity in response to a treatment with a Csnk2 inhibitor. The invention therefore relates to an inhibitor of Csnk2, for use in the treatment of microbiome dysregulations notably associated with circadian clock disruption. Said inhibitor may be selected among chemically synthesized or natural selective Csnk2 inhibitors such as flavones.

6 Claims, 4 Drawing Sheets

Figure 1:
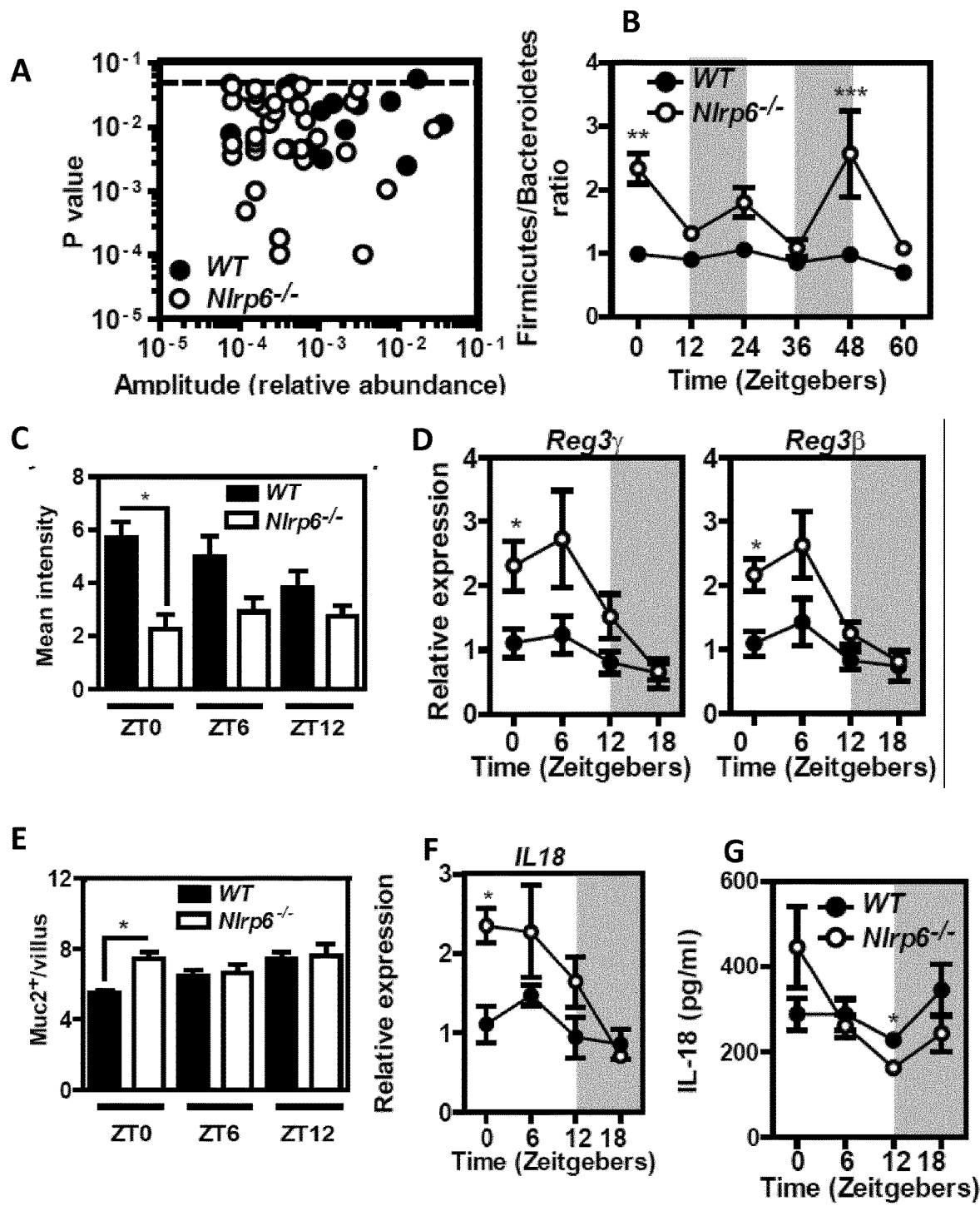

Specification includes a Sequence Listing.

METHODS AND PHARMACEUTICAL COMPOSITIONS FOR TREATING MICROBIOME DYSREGULATIONS ASSOCIATED WITH CIRCADIAN CLOCK DISRUPTION

FIELD OF THE INVENTION

The present invention relates to methods and pharmaceutical compositions for use in the treatment of microbiome dysregulations and in particular in the treatment of microbiome dysregulations associated with circadian clock disruption.

BACKGROUND OF THE INVENTION

Over millions of years of coevolution, the adaptation of gut microbial communities (the microbiota) to their nutrient-rich environment has contributed to the host's overall fitness. This highly complex microbial ecosystem has been underestimated in its importance until recently, when a detailed view of the diversity of the gut microbial communities (the microbiota) has been revealed.

The gut microbiota represents one of the densest ecosystems on Earth which has adapted from the earliest days of life to an environment shaped by the complex interplay between intrinsic and extrinsic mechanisms, including hygiene, gender, aging, drug intake and feeding behavior (1). Around 500-1,000 different bacterial species may be present in the gut of a given human individual. The colon is the most densely populated compartment, with bacterial numbers reaching in humans about $10^{11}$-$10^{12}$ cells per gram of content.

Such microbiota maintains important physiological functions such as digestion and immune regulation, thereby increasing the host's overall fitness. The microbiome performs myriad functions protecting the host against several pathologies. Indeed, the host-microbiota symbiosis has evolved in at least three directions. First, colonization by commensal microorganisms is key to immune development. Second, the commensal community keeps in check invading pathogens and prevents them from being virulent. Third, the intestinal microbiota appears to digest glycans and regulate fat storage in mice and potentially in humans.

Instability in the gut microbiota and therefore in the gut microbiome (known as dysbiosis) has been linked to the pathogenesis of several common human immunopathologies, such as cancer, autoimmune and inflammatory disorders whose incidence and socio-economic impacts are increasing. Consequently, several functional defects of the host-microbe mutualism at both the immunological and metabolic levels have been reported leading to the growing awareness of the importance of the gut microbiome in health and disease.

Diurnal oscillation in the composition of gut microbiota has recently been observed (2), which coincides with time-of-day variation in the self-renewal of the epithelium (3). Conversely, several clock-based intestinal functions are abrogated in germ-free mice (4,5). Such rhythms characterize cyclic physiological changes following a roughly 24-hour cycle.

The rhythms are maintained by the circadian clock, which is an intrinsic, self-sustained, time-tracking molecular machinery allowing most living organisms to anticipate regularly reoccurring physiological patterns. Yet the clock machinery is also able to adapt to environmental changes (6). Disturbances of the aforementioned time-tracking system have potentially broad implications for human health as epidemiological studies have shown a link between conditions disturbing day-night cycles and a variety of chronic inflammatory diseases (8), such as colorectal cancer, metabolic syndrome and IBD.

It has further been shown that this disruption of the host circadian clock by either genetic disruption or time shift is responsible for microbiota dysregulations, also referred as dysbiosis (Thaiss et al., 2014; Liang et al., 2014) that may subsequently contribute to the development of several chronic diseases, such as IBD. It is indeed worth noting that recent genome-wide association studies have revealed several single nucleotide polymorphisms that predispose to IBD in genes involved in the circadian clock, including vitamin D receptor (VDR; rs11168249); nuclear factor, interleukin 3-regulated (NFIL3 also referred as E4BP4; rs4743820); and casein kinase type II (CSNK2; rs9267531). However, despite the high physiological relevance of the microbiome on host fitness, the molecular determinants underlying the circadian regulation of the microbiota are still unknown.

As chronic exposure to disruption of circadian timing duration (affects millions of people in industrialized societies worldwide, there is a strong need to develop new compounds that will be suitable for preventing or treating dysbiosis induced by disruption of the host circadian clock. In this way, it has been suggested that characterization of new post-biotic compounds inducing beneficial changes on host-microbiota interactions may be highly desirable for subjects with circadian clock disruption, and in particular in subjects suffering from dysbiosis associated with circadian clock disruption.

SUMMARY OF THE INVENTION

The inventors of the present application reported that Nod-like receptor protein 6 (Nlrp6) preserves clock-based intestinal crypt homeostasis through direct interaction with the casein kinase 2 (Csnk2).

They showed that severe clock misalignments in intestinal cell lineage specification lead to accumulation of oscillating bacterial genera in Nlrp6-deficient mice and demonstrated that mechanistically, loss of Nlrp6 abrogates rhythmic nuclear shuttling of Csnk2 at the expense of the renewal of crypt base columnar cells.

The inventors further demonstrated that systemic inhibition of Csnk2 activity by an inhibitor of Csnk2 represses expansion of proliferating progenitors though functional Nlrp6, while leading to changes in the gut microbiota that protect against intestinal inflammation independently of Caspase-1. Collectively, their results have shown that Nlrp6 control the microbiota composition and in particular that Nlrp6 diurnally coordinates cyclical adaptation of the gut microbiota diversity to epithelial plasticity in response to a treatment with a Csnk2 inhibitor such as a dietary flavonoid.

Therefore the present invention relates to an inhibitor of the casein kinase 2 (Csnk2) activity for its use in the treatment of microbiota dysregulations or of microbiome dysregulations, preferentially of microbiota or microbiome dysregulations that are associated with circadian clock disruption, in a subject in need thereof.

The present invention is especially useful, notably as a dietary supplementation, in a subject suffering from or at risk of a circadian rhythm sleep disorder, such as a sleep dysfunction.

Typically, the inhibitor of Cnsk2 according to the invention can be selected among flavonoids, tyrphostins and their derivatives, such as for example apigenin, luteolin, chrysin, or tyrphostin AG99.

DETAILED DESCRIPTION OF THE INVENTION

The invention provides methods and compositions (e.g.: pharmaceutical compositions) for use in the treatment of microbiota dysregulations or of microbiome dysregulations in a subject in need thereof.

More particularly, the present invention relates to an inhibitor of Csnk2 activity for use in the treatment of microbiota dysregulations or of microbiome dysregulations, notably associated with circadian clock disruption.

As used herein, the term "Csnk 2" has its general meaning in the art and refer to the casein kinase type 2 or "casein kinase 2", also known as "CK2". Accordingly, Csnk2 is a tetrameric serine/threonine-selective protein kinase composed of two α/α' catalytic subunits and two non-catalytic (i.e.: regulatory) β subunits that is evolutionarily conserved throughout the eukaryotic kingdom. This ubiquitous, highly pleiotropic and constitutively active serine/threonine kinase is responsible for the generation of a substantial proportion of the human phosphoproteome as described for example by Cozza G & Pinna L A. (Expert Opin Ther Targets. 2016; 20(3):319-40).

The term "inhibitor of the casein kinase 2 activity" according to the invention refers to a compound, natural or not, which has the capability to inhibit (partly or totally) the biological activity of the Csnk2 protein. The scope of the present invention includes all those Csnk2 inhibitors now known and those Cnsk2 inhibitors to be discovered in the future. Csnk2 inhibitors are commonly classified into three categories: (1) inhibitors that target the regulatory subunit of Csnk2 (e.g., genetically selected peptide aptamers); (2) inhibitors of the catalytic activity of Csnk2 (e.g., quinobene, TBB, DMAT, IQA); and (3) disruptors of Csnk2 holoenzymes, which are often molecules binding to the Csnk2 subunit interface and inhibit the high affinity interaction of its subunits. The Csnk2 inhibitors of each class can be any type of molecule, such as, small molecules, functional nucleic acids, peptide mimetics, antibodies (also including any antibody fragments), or aptamer peptides directed against Csnk2 and notably against the catalytic or regulatory subunits, whereby the biological activity of Cnsk2 is inhibited.

Csnk2 inhibitors can be selected from i) ATP-competitive inhibitors (also called Type I inhibitors), able to interact directly with the ATP-binding site, thus blocking the ATP access and the phosphotransferring reaction or ii) the non-competitive ATP inhibitors (allosteric inhibitors or substrate competitors), which bind to structural elements unrelated with the ATP-binding regions (such as those described in Cozza et al., Expert Opinion on Therapeutic Patents, 2012; 22:9, 1081-1097).

In some embodiments, the CK2 inhibitor is a compound as described in:

Maksym O. Chekanov, Olga V. Ostrynska, Sergii S. Tarnayskyi, Anatoliy R. Synyugin, Nadiia V. Briukhovetska, Volodymyr G. Bdzhola, Alexander E. Pashenko, Andrey A. Fokin, Sergiy M. Yarmoluk. Design, synthesis and biological evaluation of 2-aminopyrimidinones and their 6-aza-analogs as a new class of CK2 inhibitors. Journal of Enzyme Inhibition and Medicinal Chemistry 2014 October; 29(5):639-46.

Maksym O. Chekanov, Olga V. Ostrynska, Anatoliy R. Synyugin, Volodymyr G. Bdzhola, Sergiy M. Yarmoluk. Design, synthesis and evaluation of 2-phenylisothiazolidin-3-one-1,1-dioxides as a new class of human protein kinase CK2 inhibitors. Journal of Enzyme Inhibition and Medicinal Chemistry 2014 June; 29(3): 338-43.

Giorgio Cozza, Lorenzo A Pinna, Stefano Moro. Protein kinase CK2 inhibitors: a patent review. Expert Opinion on Therapeutic Patents September 2012, Vol. 22, No. 9, Pages 1081-1097.

Cozza et al, How druggable is protein kinase CK2? Med Res Rev. 2010 May; 30(3):419-62.

Zhu et al., Inhibition of protein kinase CK2 expression and activity blocks tumor cell growth. Mol Cell Biochem. 2010 January; 333(1-2):159-67.

Lopez-Ramos et al., New potent dual inhibitors of CK2 and Pim kinases: discovery and structural insights. FASEB J. 2010 September; 24(9):3171-85.

Giorgio Cozza & Lorenzo A Pinna, Casein kinases as potential therapeutic targets. Expert Opin Ther Targets. 2016 March; 20(3):319-40.

Example of Csnk2 inhibitors include non-limitatively:

Polyhalogenated benzotriazole and benzimidazole derivatives, such as TBB (TTBt, 4,5,6,7 tetrabromobenzotriazole, Ki=0.40 μM, PDB code: 1J91), TBI (TTBz, 4,5,6,7-1H-tetrabromobenzimidazole, Ki=0.30 μM, PDB code: 2OXY), DRB (5,6-dichloro-1-β-D-ribofuranosylbenzimidazole), derivative of indoloquinazolines such as IQA ([5-oxo-5,6-dihydroindolo-(1,2-a) quinazolin-7-yl]acetic acid), or the analog K25/DMAT (2-dimethylamino-4,5,6,7-tetrabromo-1H-benzimidazole, Ki=0.04 μM, PDB code: 1ZOE);

Natural compounds such as anthraquinones, flavonoids (typically flavones as described below), tyrphostins, coumarins and their derivatives, for example emodin (5,6-dichloro-1-P-D-ribofuranosylbenzimidazole (D B), 6-methyl-1,3,8-trihydroxyanthraquinone) (Ki=1.5 μM, PDB codes: 1F0Q, 3PZH, 3BQC and 3C13), quercetin (2-(3,4-dihydroxyphenyl)-3,5,7-trihydroxy-4H-chromen-4-one), resorufin, 4,4',5,5',6,6'-Hexahydroxydiphenic acid 2,6,2',6'-dilactone (ellagic acid), MNA (1,8-dihydroxy-4-nitroanthraquinone, Ki=0.78 μM), MNY (1,4-diamino-5,8-dihydroxy-anthraquinone), quinalizarin (1,2,5,8-tetrahydroxy-anthraquinone, Ki=0.06 μM, PDB codes: 3FL5, 3Q9Y, 3Q9Z), MNX (1,8-dihydroxy-4-nitro-xanthen-9-one, Ki=0.8 μM) or derivatives of hydroxycourmarines such as DBC (3,8-dibromo-7-hydroxy-4-methylchromen-2-one).

Compounds sharing a common carboxyl feature able to establish an interaction with the fundamental Lys68 of the ATP-binding site of Csnk2, such as the Novartis IQA (5-oxo-5,6-dihydroindolo-(1,2-a) quinazolin-7-yl acetic acid, IC50=0.39 μM, PDB code: 1OM1), the TBCA ((E)-3-(2,3,4,5-tetrabromophenyl)acrylic acid, Ki=0.077 μM) and their derivatives like like benzoic acid compound 26 (3,4,5 tribromobenzoic acid IC50=0.64 μM) and compound 10 ((E)-3-(3-stibonophenyl)prop-2-enoic acid, IC50=0.15 μM), or other derivatives from different scaffolds like compound 7 (5,6,8-trichloro-4-oxo-1,4-dihydroquinoline-3-carboxylic acid, Ki=0.06 μM), TID46 (2-(4,5,6,7-tetraiodo-1, 3-dioxo-1,3-dihydro-2Hisoindol-2-yl)propanoic acid, IC50=0.15 μM), and the xanthene-based compound 35 (2,3,4,5-tetrabromo-6-(6-hydroxy-3-oxo-3H-xanthen-9-yl)-benzoic acid, IC50=0.08 μM), or the CX-4945

((5-(3-Chloro-phenylamino)-benzo[c] [2,6] naphthyridine-8-carboxylicacid, IC50=0.002 µM, PDB code=3PE1).

Pyrazolo-triazine, pyridocarbazole, benzopyridoindole and indenoindole derivatives characterized by poly ring scaffolds (PDB codes: 2PVH, 2PVJ, 2PVK, 2PVL, 2PVN and 3BE9).

Non-ATP site-directed CK2 inhibitors, such as small peptides, like the one derived from the sequence of CFTR with the Phe508 deletion (IC50=15 µM), cyclic peptides and their podophyllotoxine indolo-analogs (W16, IC50=20 µM,) able to disrupt the CK2 holoenzyme architecture in vitro, as well as other compounds such as hematein (3,4,6a,10-tetrahydroxy-6,7-dihydroindeno[2,1-c] chromen-9-one, IC50=0.55 µM), benzothiazole derivatives (in particular compound 1, 2'-(4-Dimethylamino-phenyl)-3,6,3'-trimethyl-[2,6'] bibenzothiazolyl-7-sulfonic acid, IC50=0.5 µM) and inorganic polyoxometalates (POMs, IC50=0.0014 µM).

Csnk2 inhibitors according to the present invention also include, but are not limited to, the compounds of any of the formulae described in International Patent Application Nos. PCT/US2007/077464, PCT/US2008/074820, and PCT7US2009/035609, and U.S. Provisional Application Ser. Nos. 61/170,468 (filed 17 Apr. 2009), 61/242,227 (filed 14 Sep. 2009), 61/180,090 (filed 20 May 2009), 61/218,318 (filed 18 Jun. 2009), 61/179,996 (filed 20 May 2009), 61/218,214 (filed 14 Jun. 2009), 61/41,806 (11 Sep. 2009), 61/180,099 (filed 20 May 2009), 61/218,347 (filed 18 Jun. 2009), 61/237,227 (filed 26 Aug. 2009), 61/243,107 (filed 16 Sep. 2009) and 61/243,104 (filed 16 Sep. 2009), the contents of each of which are incorporated herein by reference in their entirety. CK2 inhibitors can be synthesized by methods known in the art, including methods disclosed in International Patent Application Nos. PCT/US2007/077464, PCT/US2008/074820, and PCT/US2009/035609.

In some embodiments, the CK2 inhibitor is selected from the group consisting of:

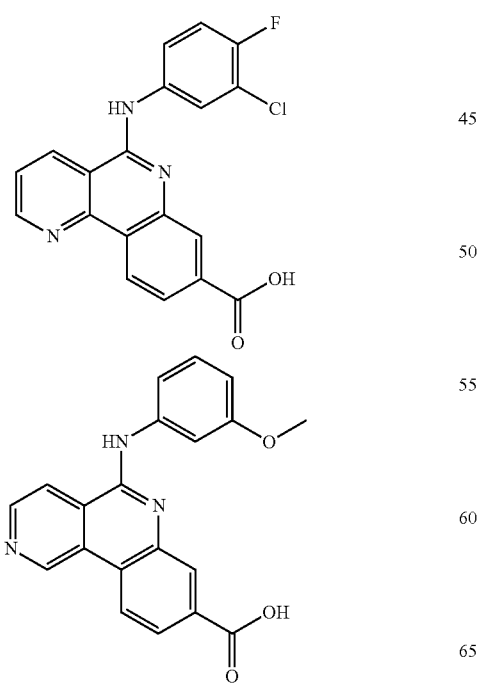

-continued

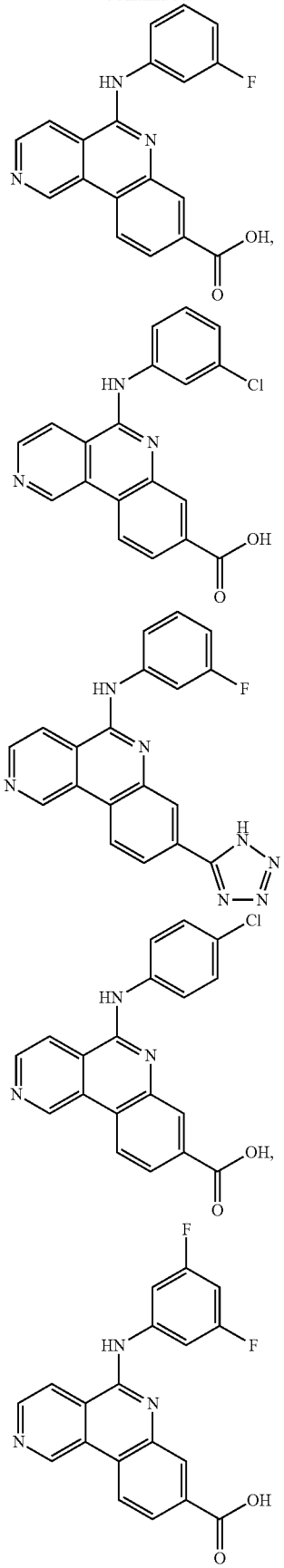

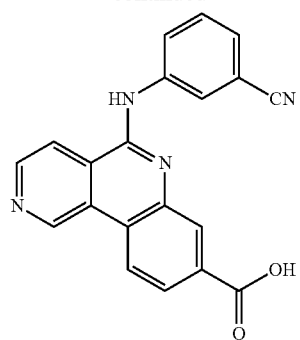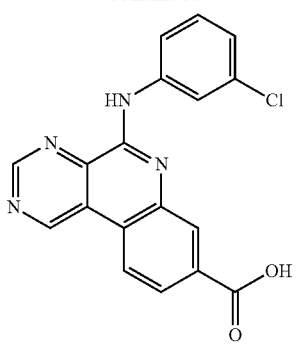

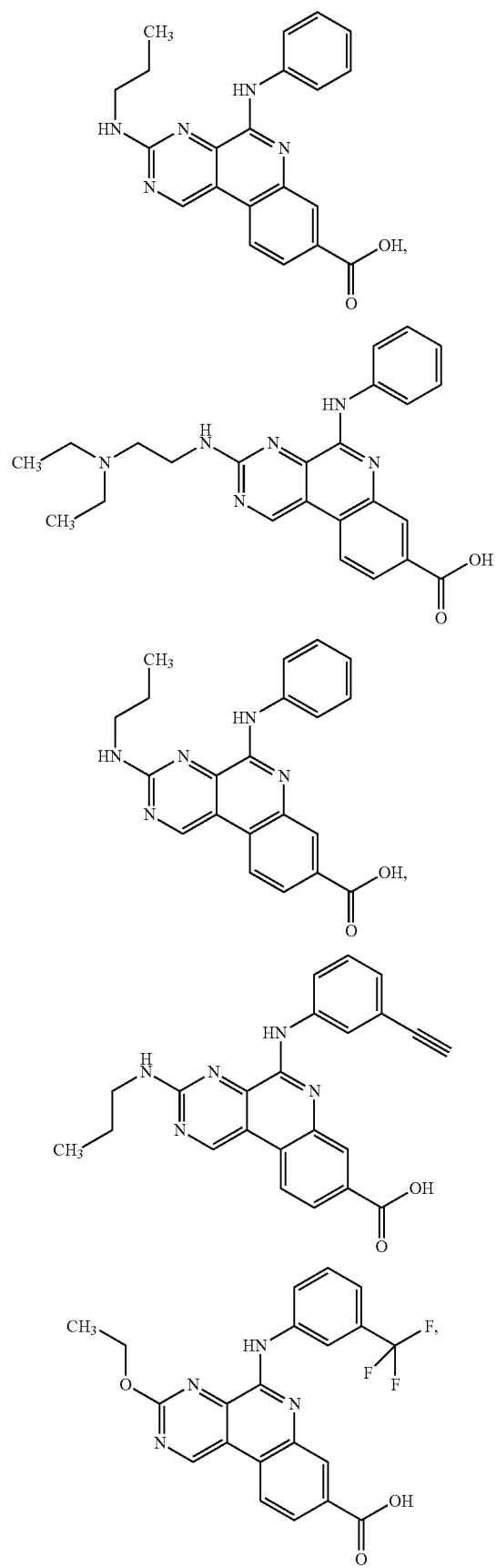
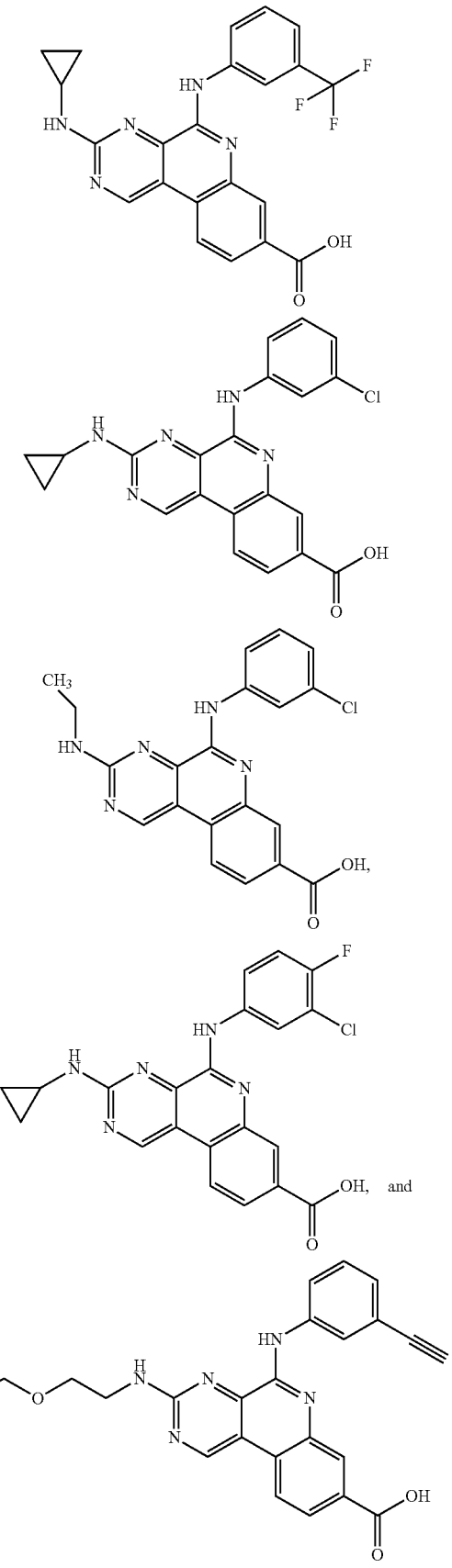

In some embodiments, the CK2 inhibitor is CX-4945:

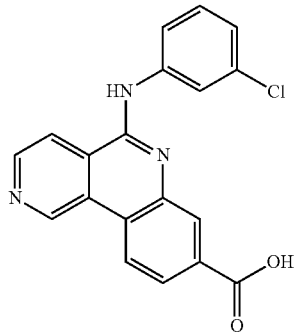 [SMILES: O=C(O)c1ccc2c(c1)nc(Nc1cccc(Cl)c1)c1ccncc12]

CX-4945 is a first-in-class potent, selective and orally available ATP-competitive inhibitor of CK2 with favorable drug properties (Siddiqui-Jain A, Bliesath J, Macalino D, Omori M, Huser N, Streiner N, Ho C B, Anderes K, Proffitt C, O'Brien S E, Lim J K, Von Hoff D D, Ryckman D M, Rice W G, Drygin D. CK2 inhibitor CX-4945 suppresses DNA repair response triggered by DNA-targeted anticancer drugs and augments efficacy: mechanistic rationale for drug combination therapy. Mol Cancer Ther. 2012 April; 11(4): 994-1005. doi: 10.1158/1535-7163.MCT-11-0613. Epub 2012 Jan. 20.).

In some embodiments, the CK2 inhibitor is a compound (Compound 1 or Compound 2) having the formula:

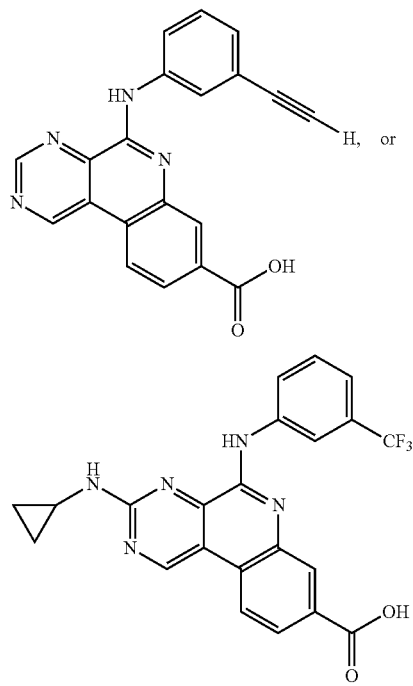

or a pharmaceutically acceptable salt or ester thereof.

In some embodiments, the CK2 inhibitor a compound described in WO 2011/013002 and in particular is selected from the group consisting of:

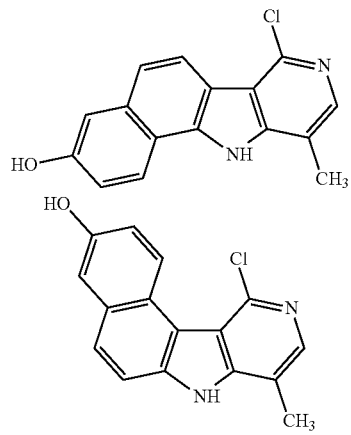

and pharmaceutically acceptable salts or esters thereof.

In some embodiments, the CK2 inhibitor is an allosteric CK2 inhibitor, i.e. a compound which does not compete with ATP but still inhibits CK2 by modifying the conformation of a CK2 subunit (e.g. CK2 alpha) in manner that the enzyme is inactive. Examples of allosteric CK2 inhibitors include but are not limited to Azonaphthalene derivatives (compound M4) as described in Moucadel V, Prudent R, Sautel C F, Teillet F, Barette C, Lafanechere L, Receveur-Brechot V, Cochet C. Antitumoral activity of allosteric inhibitors of protein kinase CK2. Oncotarget. 2011 December; 2(12): 997-1010.

In some embodiments, the allosteric CK2 inhibitor is D3.1 which has the general formula of:

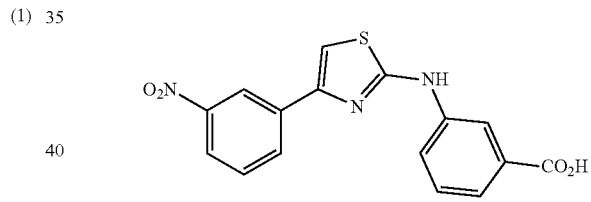

In some embodiments, the allosteric CK2 inhibitor is M4 which has the general formula of:

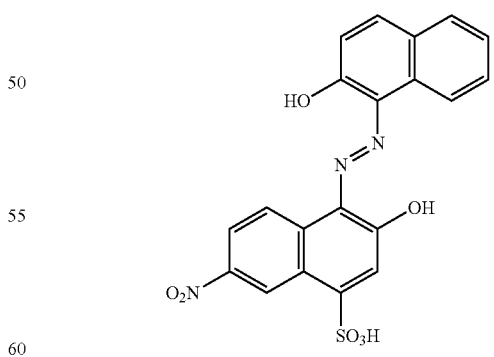

The compounds of the invention as described above can be synthesized using methods, techniques, and materials known to those of skill in the art, such as described, for example, in March, ADVANCED ORGANIC CHEMISTRY 4.sup.th Ed., (Wiley 1992); Carey and Sundberg, ADVANCED ORGANIC CHEMISTY 3.sup.rd Ed., Vols. A and B (Plenum 1992), and Green and Wuts, PROTECTIVE GROUPS IN ORGANIC SYNTHESIS 2.sup.nd Ed. (Wiley 1991). Starting materials useful for preparing compounds of the invention and intermediates thereof are commercially available from sources, such as Aldrich Chemical Co. (Milwaukee, Wis.), Sigma Chemical Co. (St. Louis, Mo.), Maybridge (Cornwall, England), Asinex (Winston-Salem, N.C.), ChemBridge (San Diego, Calif.), ChemDiv (San Diego, Calif.), SPECS (Delft, The Netherlands), Timtec (Newark, Del.), or alternatively can be prepared by well-known synthetic methods (see, e.g., Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-21, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," 3d Edition, John Wiley & Sons, 1995). Other methods for synthesis of the present compounds and/or starting materials thereof are either described in the art or will be readily apparent to the skilled artisan. Alternatives to the reagents and/or protecting groups may be found in the references provided above and in other compendiums well known to the skilled artisan. In particular, preparation of the present compounds may include one or more steps of protection and de-protection (e.g., the formation and removal of acetal groups).

Guidance for selecting suitable protecting groups can be found, for example, in Greene & Wuts, "Protective Groups in Organic Synthesis," Wiley Interscience, 1999. In addition, the preparation may include various purifications, such as column chromatography, flash chromatography, thin-layer chromatography (TLC), recrystallization, distillation, high-pressure liquid chromatography (HPLC) and the like. Also, various techniques well known in the chemical arts for the identification and quantification of chemical reaction products, such as proton and carbon-13 nuclear magnetic resonance (H and 1 3C NMR), infrared and ultraviolet spectroscopy (IR and UV), X-ray crystallography, elemental analysis (EA), HPLC and mass spectroscopy (MS) can be used as well. The preparation may also involve any other methods of protection and de-protection, purification and identification and quantification that are well known in the chemical arts.

Natural inhibitors of Csnk2 selected among anthraquinones, flavonoids, tyrphostins and their derivatives, notably among flavones, tyrphostins and their derivatives are particularly preferred according to the present invention. Additional non-limitative example of such compounds are also described in Lolli G et al. (Biochemistry 2012; 51:60-97-6107). Examples of such compounds include, in addition of the above mentioned compounds, quercetin, fisetin, kaempferol, luteolin, apigenin, chrysin, and tyrphostin AG99. Typically naringenin, naringin, hesperitin, taxifolin, galangin, biochanin A and genistein are not used as inhibitors of Csnk2 according to the invention.

In particular inhibitors of Csnk2 selected among flavone, tyrphostins and their derivatives are well suited according to the invention. Most preferably, inhibitors of Csnk2 can be selected from the group of compounds consisting in apigenin, luteolin, chrysin, and tyrphostin AG99, notably apigenin, luteolin, and tyrphostin AG99. Most preferably, an inhibitor of Csnk2 is apigenin, a prominent constituent of the human diet.

Preferably an inhibitor of Csnk2 according to the invention (natural or not) has an $IC_{50}$ of less than 10, most preferably of less than 5 µM, even more preferably of less than 1 µM for Csnk2. Preferably also the selected inhibitor is a selective inhibitor of Csnk2. Typically said selective inhibitor has an $IC_{50}$ of more than 1 µM, notably more than 10 µM for G-CK and CK1 notably CK1α.

In some embodiments, inhibition of Csnk2 activity may also be achieved through an inhibitor of Csnk2 gene expression. According to the present invention, an inhibitor of Csnk2 refers to a natural or synthetic compound that has a biological effect to inhibit or significantly reduce the expression of the gene. For example, anti-sense oligonucleotide constructs or small inhibitory RNAs (siRNAs) could be used in the present invention, as inhibitors of Csnk2 gene expression. As a matter of example single-stranded DNA/RNA chimeric oligomers or siRNA, specifically targeting Csnk2α/α' may be used (Trembley J H, Unger G M, Korman V L, et al., PLoS One 2014; 9(10):e109970; Unger G M, Kren B T, Korman V L, et al., Mol Cancer Ther 2014; 13(8):2018-29; Kren B T, Unger G M, Abedin M J, et al., Breast Cancer Res 2015; 17:19).

The microbiota refers to the totality of microorganisms that are present in or on a subject. The microbiome refers to the totality of microorganisms and their collective genetic material present in or on a subject. Microbiome dysregulations therefore directly result from microbiota dysregulation. As used herein, the term "microbiota dysregulations" or "microbiome dysregulations" preferably refers to "gut microbiota dysregulations" and "gut microbiome dysregulations" respectively. As used herein "microbiome dysregulations", notably "gut microbiome dysregulations" notably refers to dysbiosis. Dysbiosis, also named "microbial imbalance" can be defined as a deviated repertoire of the intestinal microbiota or microbiome.

A full characterization of the microbiota is still missing, notably because of the extreme complexity and variability in the composition of this microbial community within individuals. However, the bacterial component of the microbiota has been the subject of intensive studies in recent years driven by large scale projects such as the Human Microbiome Project (see Petersen et al., The NIH Human Microbiome Project. Genome Res. 2009; (12):2317-23). Metagenomic studies have established that despite the extensive interpersonal variability in community composition, there is a shared core of functionalities in the microbiome. Based on this knowledge, the literature characterizing the microbiota is exploding (see Clemente et al., Cell 2012; 148(6): 1258-70; Sartor R B, Mucosal Immunology 2011; 4(2): 127-132 see also Frank D N et Pace NR Current Opinion in Gastroenterology 2001, 17:52-57, which reviews analyses of human gastrointestinal microbiota).

Microbial imbalance in a given subject may be characterized by comparison of the microbiota of the said subject with microbiota of at least healthy subject. Distinction in the community composition may thus reveal a microbial imbalance. Analysis of microbiota may be performed on a gut microbiota sample, such as fecal sample.

Preferably, the at least one healthy subject does not suffer from any metabolic, inflammatory, immune or cancerous disease. Preferably also the at least one healthy does not suffer from circadian rhythm disorder. Typically said subject does not suffer from IBD, metabolic syndrome, diabetes or colorectal cancer. Typically also, the subject has a normal sleep pattern and a regular food intake pattern.

Also preferably, the at least one healthy subject is the same age, same sex and is from the same geographic area as the given subject. Preferably also the at least one healthy subject has the same diet (for example a Western-like diet) as the given subject. Advantageously, comparison of the gut microbiota is performed with a microbiota healthy profile of more than one healthy subject (i.e.: a healthy population).

Microbiome dysregulation(s) in a given subject may also be detected by qualitatively and/or quantitatively analyzing metabolites of a gut microbiome sample (for example a fecal sample) and comparing the obtained metabolite profile with the metabolic profile of at least one healthy subject (as defined above). As a matter of example quantitative analysis of flavone compounds (such as apigenin) in a gut microbiome sample may be performed in a given subject and the result compared with the flavone level in at least one healthy subject, preferably in a healthy population. Microbiome dysregulation can be typically characterized by a decreased level of flavone compounds in a given subject as compared to the level in at least one healthy subject.

Metabolites that may be considered to be differentially produced in the microbiome of the given subject as compared to the at least one healthy subject may be up-regulated by at least 1.5 fold, 2 fold, 3 fold, 4 fold, 5 fold, 10 fold or greater or downregulated by by at least 1.5 fold, 2 fold, 3 fold, 4 fold, 5 fold, 10 fold or greater.

In some embodiments, dysbiosis is associated with an increased levels of harmful bacteria generally associated with a reduced levels of the beneficial bacteria and/or by decreased bacterial diversity.

Non limiting example of harmful/beneficial bacteria can be:

| Harmful bacteria | Beneficial bacteria |
| --- | --- |
| *Bacteroides vulgatus,* | *Lactobacillus* species |
| *Bacteroides thetaiotamicron* | *Bifidobacterium* species |
| *Enterococcus faecalis* | Nonpathogenic *E. coli* |
| Adherent/invasive *Escherichia coli* | *Saccharomyces boulardii* |
| *Klebsiella pneumoniae,* | *Bacteroides fragilis* |
| *Bifidobacterium animalis* | *Faecalibacterium prausnitzii* |
| *Fusobacterium varium* | *Faecalibacterium prausnitzii* |
| Intestinal *Helicobacter* species | |
| Intestinal *Helicobacter* species | |
| *Ruminococcus gnavus* | |
| *Proteus mirabilis* | |

Example of harmful/beneficial bacteria are also described in Clemente et al., Cell 2012; 148(6): 125-1270; Sartor Mucosal Immunology 2011; 4(2):127-132; Schwabe F R et Jobin C, Nat Rev Cancer. 2013 November; 13(11): 800-812; Gagnière J et al., World J Gastroenterol. 2016 Jan. 14; 22(2):501-18; Keku T O et al., Am J Physiol Gastrointest Liver Physiol. 2015 Mar. 1; 308(5):G351-63.

Furthermore, as mentioned previously, the composition of gut microbiota and therefore of gut microbiome is also subjected to diurnal oscillation, which coincides with time-of-day variation in the self-renewal of the epithelium. As shown by the results included in the present application, the absence of Nlrp6 is associated with a strong accumulation of diurnally oscillating bacterial genera which led to an altered composition of the microbiota. More generally, the present data show that Cnsk2 orchestrates the well-characterized diurnal oscillation of epithelial stem cell activity through repression of Nlrp6 activity. The term microbiota dysregulations or microbiome dysregulation associated with circadian clock disruption also refers to a loss of diurnal rhythmicity of the gut microbiota or of the gut microbiome.

Therefore, in this context, subjects suffering from dysbiosis can typically be characterized by a change and/or loss of diurnal variation of the gut microbiota. Loss of microbiota diurnal rhythmicity can be detected in a subject by serial analysis of the gut microbiota over the course of the day (as for example illustrated in the results, but see also Thaiss C A. et al., Gut Microbes. 2015; 6(2):137-42 or Thaiss C A et al., Cell. 2014; 159(3):514-29).

As used herein, "circadian clock disruption" refers to disruption in a subject's circadian rhythms which usually make possible for organisms to coordinate their biology and behavior with daily environmental changes in the day-night cycle.

As used herein, the term "subject" denotes a mammal, preferably a human subject.

In some embodiment, a subject according to the invention is suffering from a circadian rhythm sleep disorder, such as advanced sleep phase disorder (ASPD), characterized by difficulty staying awake in the evening and difficulty staying asleep in the morning, delayed sleep phase disorder (DSPD), characterized by a much later than normal timing of sleep onset and offset and a period of peak alertness in the middle of the night, irregular sleep—wake rhythm, or non-24-hour sleep—wake disorder, in which the affected individual's sleep occurs later and later each day, with the period of peak alertness also continuously moving around the clock from day to day. A subject according to the invention can also be at risk of a circadian rhythm sleep disorder for example due to elderly, work nights, rotating shifts, or a disease such as Alzheimer disease, Parkinson disease, or any mental health disease.

In some embodiment, a subject according to the invention (preferably human) can also be afflicted with or be susceptible to be afflicted with dysbiosis. In a particular embodiment, the term "subject" refers to a subject afflicted with or susceptible to be afflicted with a dysbiosis that is caused by disruption of the host circadian clock.

As used herein the term "disease predisposing dysbiosis" has its general meaning in the art and refers to diseases induced by dysbiosis which is associated with disruption of the host circadian clock such as IBD, metabolic syndrome, obesity, glucose intolerance, allergies and cancers (Jones et al., 2016; Scavuzzi et al., 2016; Thaiss et al., 2014; Liang et al., 2014).

The terms "treatment", "treating" or "treat" and the like refer to obtaining a desired pharmacological and/or physiological effect. This effect is notably therapeutic in terms of partial or complete improvement or cure of the disease and/or adverse effects attributable to the disease. Treatment covers any treatment of the disease in a mammal, particularly a human, aimed at inhibiting the disease symptom, (i.e., arresting its development) or relieving the disease symptom (i.e., causing regression of the disease or symptoms). The terms "treatment", "treating" or "treat" and the like also refer to obtaining a desired pharmacological and/or physiological prophylactic effect in terms or completely or partially preventing the disease or a symptom thereof. It covers therefore any treatment of the disease in a mammal, particularly a human, aimed at preventing the disease or symptom from occurring in a subject which may be at risk, or predisposed to the disease or symptom but has not yet been diagnosed as having it.

In particular, the term "treatment of the microbiota dysregulations" or "treatment of the microbiome dysregulations" notably includes restoration of the diurnal rhythmicity of the beneficial functionality of the gut microbiota or of the gut microbiome and/or decrease in the proportion of harmful bacteria notably harmful gut bacteria.

Furthermore, the data obtained by the inventors collectively show that inhibition of Csnk2 regulates metabolic functions and reduces intestinal inflammation. As a matter of example, their data demonstrate that wild-type mice on LD cycles (12 hours light/12 hours dark) treated with an inhibitor of Csnk2 had less severe body-weight loss upon oral administration of dextran sodium sulfate (DSS), as a pre-clinical model of colitis. Also, a reduced infiltration of inflammatory cells was markedly evidenced on representative haematoxylin and eosin-stained sections of the colon from Csnk2 inhibitor-treated mice when compared to controls.

Therefore the term "treatment of the microbiota dysregulations or of the microbiome dysregulations" can also refer to the prevention of microbiota dysregulations or of microbiome dysregulations. Such prevention and notably diurnal prevention is of particular interest in a subject suffering from, or at risk of circadian rhythm sleep disruption. An inhibitor of Csnk2 may also be used as a prophylactic treatment in healthy patients. Preferably said healthy patient are at risk of circadian rhythm disorders, or are at risk of suffering from an inflammatory disease, an immune disease, a metabolic disease or a cancer. Said risk may be established based on pathogenic family history or hygiene and dietary habits.

In some embodiments of the present invention, the term "treatment of the microbiota dysregulations" can also refer to the prevention of several illnesses associated with circadian rhythm disruption and in particular of illness induced by microbiota dysregulations associated with circadian rhythm disruption, such as colorectal cancer, metabolic syndrome and IBD. An inhibitor of CK2 according to the present invention may therefore be used in subject at risk of colorectal cancer, metabolic syndrome and IBD, for example due to the pathogenic family history, or diet regimen, or in prevention of colorectal cancer relapse.

The term "treatment of the microbiota dysregulations" also refers to the maintenance of a healthy condition, in particular of normal physiological digestive and immune functions.

In this context, an inhibitor of Csnk2 according to the present invention may be used as a dietary supplement in the absence of any pathological symptom and notably in the absence of any digestive of immune symptom in order to keep physiological digestive and immune regulation.

The inhibitor of Csnk2 gene expression or the Csnk2 inhibitor may be administered in the form of a pharmaceutical composition. Preferably, said inhibitor is administered in a therapeutically effective amount.

By a "therapeutically effective amount" it is meant a sufficient amount of the inhibitor of Csnk2 gene expression of the Csnk2 inhibitor to treat and/or to prevent microbial dysregulations at a reasonable benefit/risk ratio applicable to any medical treatment.

In some embodiments of the invention, by a "therapeutically effective amount" it is also meant a sufficient amount of the inhibitor of Csnk2 gene expression or of the Csnk2 inhibitor to prevent several illnesses associated with circadian rhythm disruption and in particular of illness induced by microbiota dysregulations that are associated with circadian rhythm disruption.

In some embodiments of the invention, by a "therapeutically effective amount" it is also meant a sufficient amount of the inhibitor of Csnk2 gene expression or of the Csnk2 inhibitor to maintain the subject in a healthy condition, in particular to maintain normal physiological digestive and/or immune functions in the said subject.

It will be understood that the total daily usage of the compounds and compositions of the present invention can be decided by the attending physician within the scope of sound medical judgment. The specific therapeutically or dietary regimen for any particular subject may depend upon a variety of factors including the disorder or the dysregulation to be treated or prevented and its severity; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved.

By "therapeutic or dietary regimen" is meant the pattern of dosing used during therapy. A therapeutic or a dietary regimen may include an induction regimen and a maintenance regimen. The phrase "induction regimen" or "induction period" refers to a therapeutic or a dietary regimen (or the portion of a therapeutic or a dietary regimen) that is used for the initial treatment. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic or a dietary regimen (or the portion of a therapeutic or a dietary regimen) that is used for the maintenance of a subject during treatment of disorder or a dysregulation, e.g., to keep the subject in remission, or in good health for long periods of time (months or years). A maintenance regimen may employ continuous therapy (e.g., administering a drug at a regular intervals, e.g., daily, weekly, monthly, yearly, etc.) or intermittent therapy (e.g., interrupted treatment, intermittent treatment, treatment at relapse).

The inhibitor of Csnk2 gene expression or the Csnk2 inhibitors for use according to the present invention may be combined with pharmaceutically acceptable excipients, and optionally sustained-release matrices, such as biodegradable polymers, to form therapeutic or dietary compositions.

In the pharmaceutical of dietary compositions of the present invention, the active principle, alone or in combination with another active principle, can be administered in a unit administration form, as a mixture with conventional pharmaceutical or physiological supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Preferably, suitable administration is performed through oral or rectal route.

Preferably, the pharmaceutical composition contains vehicles which are pharmaceutically or physiologically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria, viruses and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The inhibitor of Csnk2 gene expression or the Csnk2 inhibitor or the invention can be formulated into a composition in a neutral or salt form. Pharmaceutically or physiologically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the compositions can be brought about by the use in the compositions of agents delaying absorption, for example, aluminium monostearate and gelatin.

Upon formulation, solutions will be administered in a manner compatible with the dosage formulation and in such amount as is therapeutically effective. The formulations are easily administered in a variety of dosage forms, for example through drug release capsules and the like, other pharmaceutically or physiologically acceptable forms include, e.g. tablets or other solids for oral administration; liposomal formulations; time release capsules; and any other form currently used.

The present invention also relates to a method of treating microbiota dysregulations, including those associated with circadian clock disruption, comprising the administration of an inhibitor of Csnk2 as described above to a subject in need thereof.

The present invention also relates to a method for the maintenance of a good health and/or for keeping physiological digestive and immune regulation comprising administering to a subject of dietary supplement comprising an inhibitor of Csnk2 as described above. Said dietary supplement may be administered according to a dietary regimen as described previously. For example, said systemic supplementation with Csnk2 inhibitor may be administered at specific time during the day, notably when the absorption of dietary Cnsk2 inhibitors is less effective.

In some embodiment the subject is suffering from or is at risk of a circadian rhythm sleep disorder.

In some embodiment, the dietary supplement is administered in the absence of any pathological symptom and notably in the absence of any digestive or immune symptom.

The invention will be further illustrated by the following figures and examples. However, these examples and figures should not be interpreted in any way as limiting the scope of the present invention.

FIGURES

FIG. 1: Accumulation of diurnally oscillating bacteria coincides with cyclic expression of antimicrobial peptides and interleukin-18 in Nlrp6-deficient mice. A. Relative abundance of a bacterial OTU that is oscillating within the gut microbiota of wild-type (n=5 per ZT) and Nlrp6-deficient (n=6 per ZT) mice. B. Circadian oscillations of the Bacteroidetes/Firmicutes ratio in wild-type (n=5 per ZT) and Nlrp6-deficient (n=6 per ZT) mice over 3 consecutive days. C. Mean intensity of Lysosyme-positive signals in mucosal area of wild-type (n=4 per ZT) and Nlrp6$^{-/-}$ (n=4 per ZT) mice. D. Antimicrobial gene expression in ileal tissue of wild-type (n=4-5 per time point) and Nlrp6$^{-/-}$ (n=5-6 per time point) mice. E. Number of Muc2-positive cells within the mucosal area of wild-type (n=4 per ZT) and Nlrp6$^{-/-}$ (n=4 per ZT) mice. F. IL-18 protein levels in colonic tissue explants of wild-type (n=4-5 per time point) and Nlrp6$^{-/-}$ (n=5-6 per time point) mice. G. Relative IL-18-encoding gene expression in colonic tissue of wild-type (n=4-5 per ZT) and Nlrp6$^{-/-}$ (n=5-6 per ZT) mice. Black and white symbols represent wild-type and Nlrp6$^{-/-}$ mice respectively. Scale bar represents 100 mm. Error bars show SEM. *p≤0.05 **p≤0.01.

Figure 2:
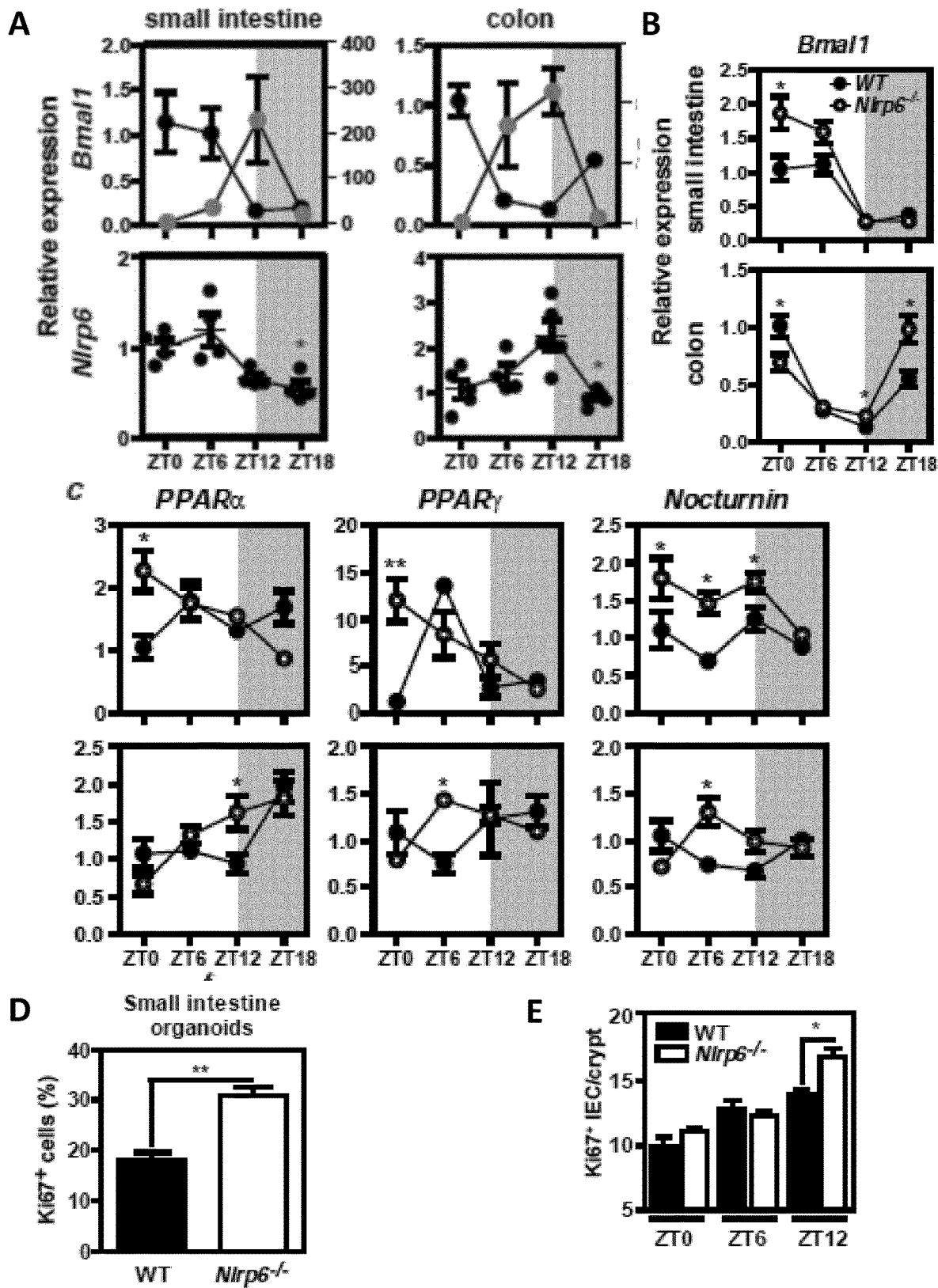

FIG. 2: Cyclic epithelial Nlrp6 expression regulates circadian clock. A. Oscillation of transcript level for Nlrp6, Bmal1 and Dbp in the colon and the small intestine of wild-type mice (n=5). B,C. Gene expression in small intestinal tissue of wild-type and Nlrp6$^{-/-}$ mice (n=5). D. Representative pictures of immunofluorescent staining in small intestinal organoids. Scale bar represents 50 μm. E. Representative pictures of Ki67 immunostaining in colonic tissue samples. Scale bar represents 100 mm. Black and white symbols represent wild-type and Nlrp6$^{-/-}$ mice respectively. Error bars show SEM. *p≤0.05 **p≤0.01.

Figure 3:
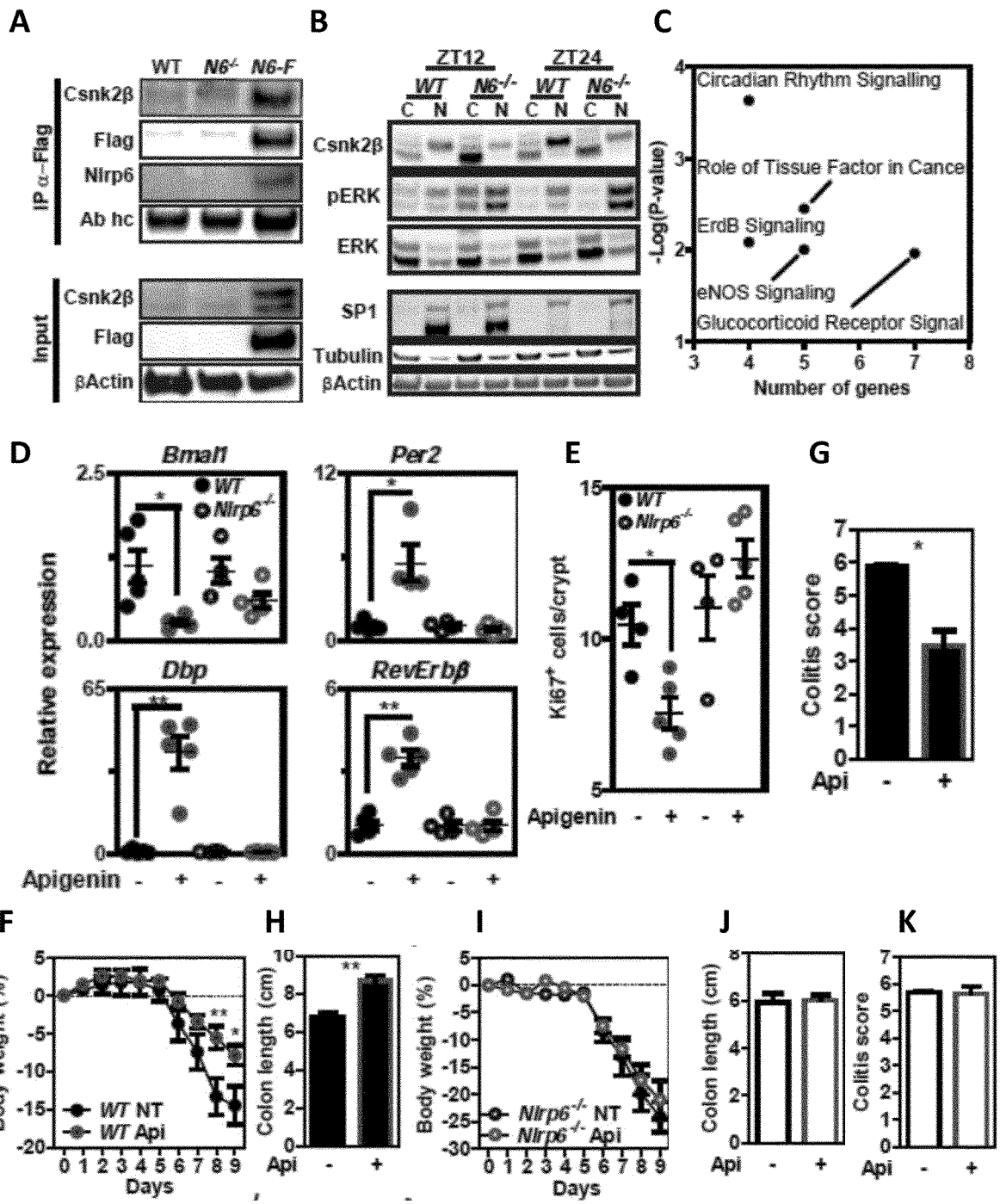

FIG. 3: Nlrp6 regulates chronobiology of epithelium self-renewal through the casein kinase 2. A, Co-immunoprecipitation of Nlrp6-3xFlag-GFP protein in ileal tissue with FLAG Ab. B, Nuclear (N) and cytoplasmic (C) extracts from wild-type and Nlrp6-deficient MEFs at ZT12 and ZT24 were subjected to Western blot analysis using anti-CNSK2, anti-pERK and anti-ERK antibodies. The results shown are representative of two independent experiments. C, Top 5 signaling pathways as a result of 3-week regimen of apigenin (750 μg/mouse, twice a week). Numbers of differentially expressed genes are depicted for each enriched pathways. D, Clock gene expression in colonic tissue of vehicle-treated and apigenin-treated mice. E, Average numbers of Ki67+ cells per colonic crypt. F, Body weight loss of wild-type (n=5) mice that were pre-treated with apigenin for 3 weeks (750 μg/mouse, twice a week) before 2% DSS administration. G, colon length. H, Histological score. I, Body weight loss of Nlrp6−/− (n=4) mice that were pre-treated with apigenin for 3 weeks (750 μg/mouse, twice a week) before 2% DSS administration. J, colon length. K, Histological score. Error bars show SEM. *p≤0.05. The results shown are representative of three independent experiments. Black and white symbols represent wild-type and Nlrp6−/− mice respectively.

Figure 4:
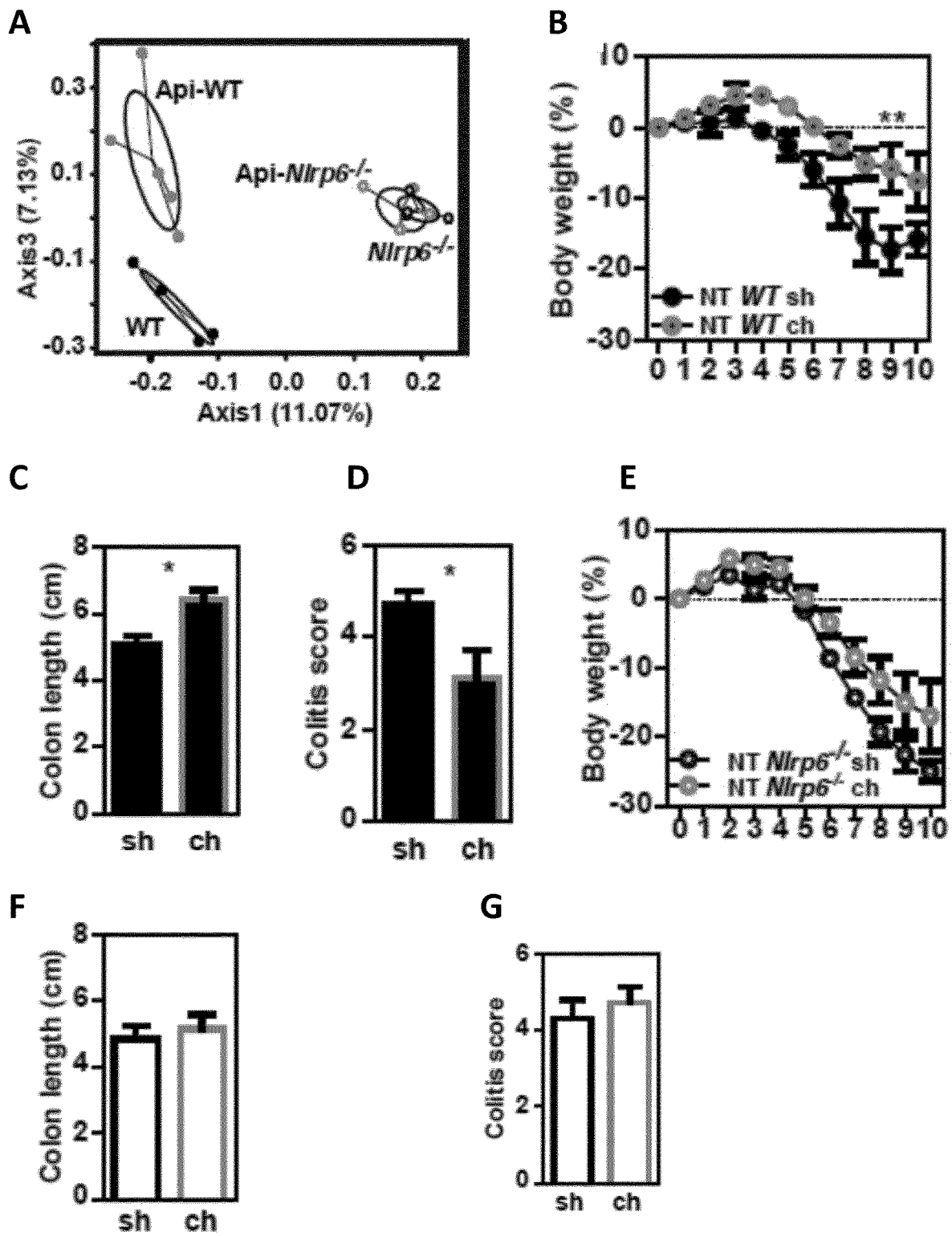

FIG. 4: The control of the gut microbiota by Nlrp6 contributes to the anti-inflammatory effect of apigenin. NT and Api mice were co-housed for 3 weeks of Api treatment. A, Principal coordinate analysis of fecal bacterial communities profiled from wild-type (n=5) and Nlrp6−/−(n=5) mice that were treated or not with apigenin. Principal coordinates were calculated on non-abundance based Jaccard distances representing community composition of compared samples. Body weight loss (B, E), colon length (C, F), and colitis score (D, G) are presented for wild-type (n=5) and Nlrp6−/− (sh n=4, ch n=5) mice. Black and white symbols represent wild-type and Nlrp6−/− mice respectively. Error bars show SEM. *p≤0.05. Scale bars represent 100 μm.

EXAMPLE

The results provided therein show that Nlrp6 supports diurnal oscillation of host-microbiota interactions through casein kinase 2. In other words, the authors demonstrated that the non-canonical Nlrp6 inflammasome regulates circadian clock through Csnk2.

Chronic exposure to disruption of circadian timing duration (e.g. night shift work or inadequate sleep) affects millions of people worldwide. Health consequences of sleep dysfunction include susceptibility to inflammatory bowel diseases through poorly understood mechanisms. Herein, we demonstrate that the Nod-like receptor protein 6 (Nlrp6) preserves clock-based intestinal crypt homeostasis through direct interaction with the casein kinase 2 (Csnk2). Severe clock misalignments in intestinal cell lineage specification lead to accumulation of oscillating bacterial genera in Nlrp6-deficient mice. Mechanistically, loss of Nlrp6 abrogates rhythmic nuclear shuttling of Csnk2 at the expense of the renewal of crypt base columnar cells. Conversely, inhibition of Csnk2 activity by the flavonoid apigenin represses expansion of proliferating progenitors though functional Nlrp6, while leading to changes in the gut microbiota that protect against intestinal inflammation independently of Caspase-1. Collectively, Nlrp6 diurnally coordinates cyclical adaptation of the gut microbiota diversity to epithelial plasticity in response to dietary flavonoids.

Abbreviations list. ANOSIM: ANalysis Of SIMilarity, Arntl: Aryl Hydrocarbon Receptor Nuclear Translocator-Like, Csnk2: Phosvitin/casein kinase type II, DSS: Dextran Sodium Sulfate, IECs: intestinal epithelial cells, eGFP: enhanced Green Fluorescent Protein, ERK1/2: extracellular signal-regulated kinases 1 and 2, IBD: inflammatory bowel diseases, LD: 12 hours light/12 hours dark, MEFs: mouse embryonic fibroblasts, Nlrp6: Nucleotide binding oligomerization domain (NOD)-like receptor 6, OTUs: operational taxonomic units, Ppar-alpha: peroxisome proliferator-activated receptor alpha, Ppar-gamma: peroxisome proliferator-activated receptor gamma, Rora, RAR-related orphan receptor A, rRNA: 16S ribosomal RNA, ZT: Zeitgeber.

Material & Methods

Mice and reagents. The Nlrp6-3xFlag-IRES-eGFP mouse was generated at the Institut Clinique de la Souris (Illkirch, France; further details available upon request). Age- and gender-matched Nlrp6-deficient (Nlrp6−/−) and control C57BL6/J mice had free access to a standard laboratory chow diet in a half-day light cycle exposure and temperature-controlled environment. All animal studies were approved by the local investigational review board (CEEA232009R) in an accredited establishment (N° B59-108) according to governmental guidelines N° 86/609/CEE. The experimental model of colitis was performed as previously described 10. Tissue and blood sampling was performed under LD conditions, with ZT0 being the start of the light period (8 a.m.) and ZT12 the vespertinal crepuscule (8 p.m.). Apigenin (750 μg/mouse; Santa Cruz) was intraperitoneally given twice a week at ZT6 for 1 or 3 weeks period.

Isolation of primary IECs, generation and culture of immortalized mouse embryonic fibroblasts. Primary IECs and lamina propria mononuclear cells (LPMCs) were isolated from the distal ileum and colon as described previously 31. CD11b+ LPMCs were enriched by Miltenyi kit following the manufacturer's instructions. For fibroblast isolation, IECs were isolated and discarded and the remaining tissue was collected and washed in PBS. Using sterile scalpel colonic tissue was cut in small pieces (25-30 pieces). At the bottom of the standard cell culturing dish the network was engraved by sterile scalpel and the tissue pieces were placed at the net junctions with the luminal side down. The dishes were left for 20 min to dry and allow tissue to attach to the dish bottom and the culturing medium DMEM, 10% FCS supplemented with 5% penicillin/streptomycin was carefully added. Dishes were incubated at 37° C., 5% CO2. For next five days medium in the dishes was daily changed for fresh DMEM, 10% FCS, 2.5% penicillin/streptomycin and after that 2 times per week for fresh DMEM, 10% FCS, 1% penicillin/streptomycin. The presence of individual cells that came out of the tissue parts was monitored daily. Big, star-shaped fibroblasts were first noticed after 5 days of culture. After total 3 weeks of culturing tissue parts were removed from the dishes, suspension cells were washed away with PBS and attaching cells detached by 2 times incubation with Trypsin/EDTA 5 min, 37° C. Attaching cells were pelleted at 400×g for 3 min and transferred to the cell culturing flask in DMEM, 10% FCS, 1% penicillin/streptomycin. Cells were passaged two times per week and used for further manipulation at the passage 4. Immortalized mouse embryonic fibroblasts (MEFs) were generated from embryos that were obtained on embryonic day E13.5 to 14.5 from uterine horns of pregnant Nlrp6-deficient and wild-type females. Placenta and yolk sac were removed from each embryos that were eviscerated and decapitated before digestion with ice-cold 0.25% trypsin/EDTA for 20 minutes at 37° C. After neutralizing trypsin digestion, suspended cells were passed through an 100M filter and cultured on 0.1% gelatin-coated flasks with DMEM culture medium (Life technology) supplemented with 10% FBS, non-essential amino acids and antibiotics. Immortalized (MEFi) were used with over 25 passages. MEFi (0.08×106 cells) were seeded in triplicate in 6-wells plate in DMEM Glutamax medium (Life technologies) containing 2% ITS-A (Life technologies)+2% FBS 24 h before experiment. Every 24 h hours during 7 days, cells were collected by trypsinization and counted using Countess® device according to manufacturer instructions (Life technologies). MEFs synchronization was performed as described previously 32. The chemically synthesized organic compound U0126 was used at 20M (Sigma-Aldrich).

Intestinal organoid formation and immunofluorescent staining. Small intestinal crypts were isolated as previously described 33. Five hundred crypts/wells were seeded in round bottom plates embedded in 10 µl/well growth factor reduced matrigel (Corning). After 20 min incubation at 37° C., 5% CO2 crypts were overloaded with 100 µ/well of crypt medium as previously described 33. The medium was exchanged every 4 days. At day 6 after seeding, the organoids were recovered from the matrigel adding Cell Recovery solution (BD Bioscience) then treated with 0.8 U/µl DNase and 0.3 U/µl dispase in HBSS to obtain single cells. Cell suspension was then stained with AF488-conjugated Live/dead staining (Life Technologies), fixed, permeabilized and incubated with anti-Ki67 eFluor660 Ab (clone SolA15, eBioscience). Cells were then aquired on BD FACS Canto II and results analysed by FlowJo software. For the immunofluorescent staining, the organoids were fixed with 4% PFA and embedded in 4% low melting agarose as already described 34. 150 mm sections were obtained by using a HM650V vibratome (Thermo Fisher Scientific). Antibody anti-Ki67 efluor660 clone:SolA15 (eBioscience) and AF488-conjugated Phalloidin (Life Technologies) were used. Nuclei were stained by DAPI (1 µg/ml, Life Technologies). Sections were mounted with ProLong Gold Antifade reagent (Life Technologies). Images were acquired using Opterra Multipoint Scanning Confocal Microscope (Bruker).

Immunohistochemistry, Immunofluorescence and histological analysis. Intestinal tissue was fixed in formalin, dehydrated in series of increasing concentration of alcohols and toluene before being embedded in paraffin. For immunohistochemistry, 5 µm-thick tissue sections were placed on Superfrost Plus slides (Thermo Scientific), incubated for 10 min at 60° C. and rehydrated through a series of graded alcohols and distilled water. Endogenous peroxidases were blocked by 3% hydrogen peroxide for 10 min. Antigen retrieval was performed in citrate buffer (10 mM, pH 6) by steaming sections in a microwave oven for 20 min. Tissue sections were blocked with 5% BSA/PBS for 30 min at RT and primary Ab against either Ki67 (1:100, ab15580, Abcam), M2 Ab to Flag (1:100, F3165, Sigma) or cleaved caspase3 (1:50, 9661, Cell Signalling) was directly applied and incubated one hour at room temperature (RT) or overnight at 4° C. Slides were washed 3× in PBS before applying either secondary peroxidase-conjugated goat anti-rabbit IgG (1:100, Interchim) or peroxidase conjugated goat anti-mouse IgG (1:100, Interchim) Ab two hours at RT. Targeted antigens were visualized by using 3.3'-diaminobenzidine solution (BD Pharmingen) followed by nuclear counterstain with hematoxylin. Immunofluorescence staining procedure was done by incubation overnight at 4° C. of primary antibody against Lysozyme (A0099, Dako) at 1:1000 according to the protocol provided by Cell Signalling Technology. Secondary Ab (1:200, A11008, Life Technologies) was applied for 1 hour at RT followed by nuclear counterstain with DAPI. Tissue sections were covered by using ProLong® Gold Antifade reagent (Life Technologies). Microscopic analyses were performed by using the Zeiss Axioplan 2 imaging microscope, Axio Imager Z1 microscope, Axiovision software (all from Zeiss, Oberkochen, Germany), and ImageJ software. Staining of cryosections (5 m) was performed to stain GFP on colonic tissue according to manufacturer's instructions (Cell Signaling Technology). Polyclonal rabbit anti-GFP Ab (1/1000, Molecular Probes) and monoclonal rat anti-integrin 6 Ab (1/100, BD Pharmingen) were used as primary Abs and incubated together on the samples for 3 hours at RT. Secondary AF488-coupled goat anti-rabbit Ab and AF594-coupled goat anti-rat Ab (1:500, Molecular Probes) applied for 1 hour at RT followed by counterstain with DAPI. Sections were covered with Mowiol.

Two-hybrid screening, co-immunoprecipitation and western-blotting. The bacterial two-hybrid screening was performed according to manufacturers' instructions (Agilent technologies). Distal ileal tissue samples were lysed in PY buffer (50 mM Tris-HCl, 150 mM NaCl, 5 mM EDTA, 1% (v/v) Triton X-100, pH=8) supplemented with complete protease inhibitors (Roche). Recombinant protein G Sepharose (Life Technologies) and mouse anti-flag M2 Ab (Sigma-Aldrich) were used to precipitate Nlrp6 protein from total tissue proteins of Nlrp6-3xFlag-IRES-eGFP mice. Proteins for western-blotting were isolated by lysing the MEF cells in Ripa buffer (10 mM Tris-HCl, 150 mM NaCl, 1% (v/v) Triton X-100, 0.1% (w/v) SDS, 0.5% (w/v) Na-deoxycholate) supplemented with complete protease inhibitors (Roche). Protein concentration was measured by Pierce BCA kit (Thermo Fisher) and 10 µg of proteins in Blot LDS Sample Buffer and Blot Sample Reducing Agent were loaded on Blot 4-12% Bis-Tris Plus gel (Life Technologies). iBlot2 and NC Regular Stocks were used for transfer of samples to the membrane and 5% milk solution for blocking and Ab dilution. The following primary Abs were used: rabbit anti-• Actin (Interchim), rabbit anti-Csnk2 Sigma), rabbit anti-phospho ERK1/2 (Cell Signalling), rabbit anti-ERK1/2 (Cell Signalling), mouse anti-Flag M2 (Sigma), goat anti-Nlrp6 E20 (Santa Cruz), rabbit anti-SP1 (Santa Cruz) and mouse anti-tubulin (Cell Signalling). Peroxidase-conjugated donkey anti-goat IgG Ab (Santa Cruz), peroxidase-conjugated goat anti-mouse IgG Ab (Interchim) and peroxidase-conjugated goat anti-rabbit IgG Ab (Interchim) were used as secondary Abs.

Tissue explant analyses. Distal colonic tissue part (0.5 cm long) was open longitudinally and washed well in PBS to discard faeces and debris. The tissue was incubated in DMEM GlutaMax, 10% FCS (v/v), 1% (v/v) penicillin/streptomycin and left at 37° C., 5% CO2 for 8 h. IL-18 was measured in the medium by ELISA according to manufacturer's instructions (MBL).

Gene expression and microarray analysis. Isolated RNA was reverse-transcribed with the cDNA synthesis kit (Agilent Technologies), according to the manufacturer's instructions. The resulting cDNA (equivalent to 5 ng of total RNA) was amplified using the SYBR Green real-time PCR kit and detected on a Stratagene Mx3005P (Agilent Technologies). RT-PCR was performed forward and reverse primers (sequences available upon request). On completion of the PCR amplification, a DNA melting curve analysis was carried out in order to confirm the presence of a single amplicon. Actb was used as an internal reference gene in order to normalize the transcript levels. Relative mRNA levels (2-Ct) were determined by comparing (a) the PCR cycle thresholds (Ct) for the gene of interest and Actb (ΔCt) and (b) ΔCt values for treated and control groups (ΔCt). Microarray analysis on IECs that were isolated from apigenin- or vehicle-treated mice was performed as previously described10. Gene ontology analysis was performed as described previously using the two-sided Fisher's exact test28. Biological processes associated with the genes of interest were retrieved from the Gene Ontology Consortium (http://www.geneontology.org).

Microbiota analysis. 16S rRNA gene variable region V3 and V4 was amplified using dual indexed fusion primers, in brief primers consist of illumina linker sequence, 12 base barcode sequence and heterogeneity spacer followed by either 16S rRNA gene specific forward (319F: ACTCCTACGGGAGGCAGCAG; SEQ ID NO: 1) or reverse (806R: GGACTACHVGGGTWTCTAAT; SEQ ID NO: 2) primer sequences 29. DNA was amplified using above mentioned composite primers in duplicate in a GENEAMP™ PCR system 9700 (Applied Biosystems, Foster City, Calif., USA) using the following cycling conditions: an initial denaturation of 3 min at 98° C. followed by 30 cycles, denaturation at 98° C. for 10 seconds, annealing at 50° C. for 30 seconds and elongation at 72° C. for 30 seconds. Final extension was at 72° C. for 10 minutes. Amplified product was run on agarose gel to assess the amplicon size and amplification performance. Amplicons quantities were normalized using SEQUALPREP™ kit (Invitrogen) and pooled as a single library. Sequencing was performed using Illumina MiSeq using 2×300 sequencing kit with standard HP10 and HP11 primers. Sequencing reads were primarily processed for quality control using the software MOTHUR. Forward and reverse reads were assembled to form contigs, reads not having perfectly matched specific primers and barcodes, having any ambiguous base and more than 8 homopolymers were removed from downstream analysis. Sequences not aligning to desired bacterial V3-V4 variable regions, suspected chimera and likely to be of non-bacterial origin were detected and removed. Sequences with at least 97% similarity were clustered in into Operational Taxonomical Units (OTUs). These OTUs were classified taxonomically using Mothur modified RDP reference and taxonomy database30. Principle coordinate analysis (PcoA) was performed on Jaccard distances among communities. Principle coordinates were visualized using rgl with in R application package (www.r-project.org). Indicator analysis was performed to identify prominent OTUs contributing to the differences between analysed groups. Non parametric Shannon index of diversity was calculated as a measure of alpha diversity index. Statistical differences were determined by non-parametric Mann-Whitney Test.

Statistics. Data were analysed using Prism4.0 (GraphPad Software, San Diego, Calif.). The non-parametric Kruskal-wallis test with Dunn's multiple comparison test, the non-parametric Mann-Whitney test or the parametric one-way ANOVA test with Bonferroni's multiple comparison test were used. JTK_cycle algorithm was implemented to detect potential cycling components at species level OTUs 12. The tool uses a non-parametric test method to detect monotony of orderning (eg. rhythm patterns) in subsets of data across ordered independent groups based on a combined Jonckheere-Terpstra-Kendall algorithm. Values represent the mean of normalized data +/−SEM. Asterisk, significant difference $P \leq 0.05$.

Results

Recent progress in high-throughput sequencing has enabled a detailed view of the architecture of the gut microbial communities (the microbiota) which have adapted from the earliest days of life to an environment shaped by the complex interplay between intrinsic and extrinsic mechanisms, including hygiene, gender, aging, drug intake and feeding behavior (1). The presence of stable ecological niches maintains important physiological functions such as digestion or immune regulation, thereby increasing the host's overall fitness. Diurnal oscillation in the composition of gut microbiota are observed as a function of feeding time, gender and several core clock components of the host (2, 3, 4), which coincides with time-of-day variation in the self-renewal of the epithelium (3). Conversely, several clock-based intestinal functions are abrogated in germ-free mice (4), including sensing of glucocorticoids by intestinal epithelial cells (IECs)(5). Such rhythms characterize cyclic physiological changes following a roughly 24-hour cycle. The rhythms are maintained by the circadian clock, which is intrinsic, self-sustained, time-tracking molecular machinery allowing most living organisms to anticipate regularly reoccurring physiological patterns. Yet the clock machinery is also able to adapt to environmental changes (6). Disturbances of the aforementioned time-tracking system have potentially broad implications for human health. About 15-20% of workers are regularly engaged in shift work schedules involving night work (7), which is potentially disturbing circadian rhythms throughout the entire work life. Epidemiological studies have shown a link between conditions disturbing day-night cycles (e.g. shift work, sleep deprivation, jet lag) and a variety of chronic inflammatory diseases (8), such as metabolic syndromes and inflammatory bowel diseases (IBD). Despite an obviously strong influence of rhythmic nutrient intake, astonishingly little is known how the interplay between IECs and the gut microbiota is regulated and how stability of such mutualistic interaction is maintained over a diurnal cycle.

The Nucleotide binding oligomerization domain (NOD)-like receptor 6 (Nlrp6) has been shown to control intestinal homeostasis by regulating the composition of the gut microbiota (9-11). To determine whether Nlrp6 may control the composition of the gut microbiota over the course of the day, we applied a nonparametric JTK_cycle algorithm for detection of cycling variables in 16S ribosomal RNA (rRNA) gene sequencing based bacterial profiles from faecal samples that were collected every twelve hours over a three-day period (12). In line with previous findings (2), the abundance of ~0.6% (42/2672) bacterial operational taxonomic units (OTUs) was found to diurnally oscillate (P value<0.05, after Benjamini-Hochberg correction, FIG. 1A). Among these rhythmically oscillating OTUs, 8 OTUs were shared between both wild-type and Nlrp6-deficient mice which were fed ad libitum under strict 12 hours light/12 hours dark (LD) conditions. Only 8 unique OTUs were shown to display an oscillatory behavior in wild-type mice. In contrast, the absence of Nlrp6 led to a strong accumulation of diurnally oscillating bacterial genera with 26 OTUs that were characterized by a significant rhythm pattern (P value<0.05, after Benjamini-Hochberg correction, FIG. 1A). Among the aforementioned cyclic OTUs, most of them were related to Clostridiales group. Consequently, the altered rhythmicity led to an altered composition of the microbiota with a stronger fluctuation of the *Bacteroides*/Firmicutes ratio (FIG. 1B) which may ultimately contribute to the known prediabetic state in Nlrp6-deficient mice (13). More importantly, rhythmic changes of transcript levels for several antimicrobial peptides were observed at the distal ileum of Nlrp6-deficient mice (not shown). Consequently, lysozyme-containing granules by Paneth cells were found less abundant in Nlrp6-deficient mice at dawn (Zeitgeber time 0, ZT0), while no differences were observed at ZT6 and ZT12 (FIG. 1C,D). This rhythmic expression pattern of the aforementioned genes in Nlrp6-deficient mice correlated with the number of Muc2-positive IECs (FIG. 1E) and the oscillation of both transcript (FIG. 1F) and protein (FIG. 1G) level of interleukin-18 that is thought to prevent prevents goblet cell maturation (14). This abnormal phase in timing could explain the accumulation of diurnally oscillating bacterial genera which together might be responsible for signs of dysbiosis in Nlrp6-deficient mice (9).

Given the night-time decrease in corticotropin-releasing hormone (also referred as corticoliberin) (5), we hypothesized that Nlrp6 expression may vary as a result of daily fluctuations of such hypothalamus-released peptide hormone which is known to repress Nlrp6 expression (15). Interestingly, on its own, variation across the circadian cycle was observed for transcript level of Nlrp6 at both distal ileum and colon (FIG. 2A). The bathyphase of Nlrp6 expression at the small and large intestine inversely correlated with rhythmic expression of Aryl Hydrocarbon Receptor Nuclear Translocator-Like (also referred as Arntl or Bmal1) (FIG. 2B) that is known to be regulated by RAR-related orphan receptor A (Rora) signalling in IECs (5). In line with the hypothesis, gene expression analysis in the distal ileum of Nlrp6-deficient mice revealed abnormal diurnal oscillations of Bmal1 (FIG. 2B) and several nuclear receptors (FIG. 2C); deregulation of which has been shown to cause metabolic syndrome (5). Notably, gene expression of peroxisome proliferator-activated receptor alpha (Ppar-alpha) and gamma (Ppar-gamma) was lowered during the "resting phase" at both distal ileum and colon of wild-type mice, but remained at the highest level in Nlrp6-deficient mice (FIG. 2C). Consistently, the small and large intestine of Nlrp6-deficient mice showed a greater expression of Nocturnin that is known to enhance the activity of Ppar-gamma (FIG. 2C). Collectively, our results revealed an exacerbated epithelial activation of nuclear receptors which may render the intestinal barrier of Nlrp6-deficient mice more prone to inflammatory responses to injury over the course of the day.

To define which cell type may express Nlrp6 at the intestinal interface with the microbiota, we generated a knock-in mouse expressing Nlrp6 with a carboxy-terminal 3xFlag Tag and an IRES-eGFP cassette (not shown). qRT-PCR analysis revealed a restricted expression of Nlrp6 to differentiated IECs (data not shown) as what reported for Ppar-gamma (16), which was confirmed by immunofluorescence and immunohistochemical analysis (data not shown). We next made use of a model of three-dimensionally cultured IECs (also known as organoids) derived from the jejunum of wild-type and Nlrp6-deficient mice. Intriguingly, loss of Nlrp6 expression in organoids resulted in an enhanced proportion of Ki67$^+$ cells (FIG. 2D). Similar findings were observed in mouse embryonic fibroblasts (MEFs) that were derived from mice deficient in Nlrp6 in which an enhanced activation of extracellular signal-regulated kinases 1 and 2 (ERK1/2) and Akt signalling was observed in response to LPS (data not shown). We next evaluated cell growth upon treatment with U0126, which is a selective inhibitor of extracellular signal-regulated kinases 1 and 2 (ERK1/2) signalling. Growth rate of U0126-treated wild-type MEFs was found comparable to the one of similarly treated Nlrp6-deficient MEFs (data not shown). A higher proliferation index of colonic IECs was also observed at vespertinal crepuscule by immunohistochemical analysis using Ki67 (data not shown), yet the number of cleaved caspase-3-positive cells was found similar between wild-type and Nlrp6-deficient mice (data not shown). Accordingly, the enhanced risk of colitis in Nlrp6$^{-/-}$ mice coincided with deregulated cycling of IECs and enhanced expression of ERK1/2-target genes involved in IEC proliferation (10). These results suggested us that rhythmic epithelial expression of Nlrp6 is likely involved in a clock-based maintenance of epithelial barrier function.

To get further insights how Nlrp6 signalling may diurnally dictate epithelial self-renewal, we performed a bacterial two-hybrid screening of a MEFs cDNA library by applying the Pyrin domain of mouse Nlrp6 as bait. Two positive overlapping clones contained a cDNA encoding for the regulatory beta subunit of Phosvitin/casein kinase type II (Csnk2β, OMIM 115441). Csnk2 is a tetrameric serine/threonine-selective protein kinase that is evolutionarily conserved throughout the eukaryotic kingdom. Intriguingly, Csnk2 is a core member of the circadian clock involved in regulation of period lengthening and stress-responsive pathways (17,18). In *Drosophila*, the andante mutant is characterized by loss of Csnk2 which results in abnormally long circadian periods (17). As predicted by our two-hybrid screening, Nlrp6 endogenously immunoprecipitated together with Csnk2 β in the intestine of mice (FIG. 3A). Given that Csnk2 translocates to the nuclear compartment upon activation (19), we next postulated that the enhanced activation of ERK1/2 signalling in the absence of Nlrp6 may result from an abnormal day-night shuttling of Csnk2 (20, 21). Consistently, diurnal oscillation of nuclear shuttling of Csnk2 β and phosphorylated ERK1/2 was found disrupted in the absence of Nlrp6 in a time-of-day dependent manner (FIG. 3B). To assess whether Nlrp6 may function downstream of Csnk2, we made use of apigenin (4',5,7-trihydroxyflavone), as a naturally occurring plant flavone that is an ATP-competitive inhibitor of the activity of Csnk2. Of note, microarray analysis revealed a specific subset of 54 genes that were differentially expressed with a Logfc of 1.5 in wild-type mice upon apigenin administration. Intriguingly, the signature of apigenin treatment was found to be enriched for genes associated with cancer and circadian rhythm signalling (FIG. 3C). Importantly, qRT-PCR analysis revealed that colonic transcript levels of several clock machinery genes were significantly influenced by apigenin administration through Nlrp6 (FIG. 3*d*). Consequently, a three-week regimen of apigenin lowered IEC proliferation as shown by Ki67 Ab staining without any change on the number of caspase-3 positive IECs (FIG. 3D). In contrast, the anti-proliferative effect of apigenin was abrogated in Nlrp6-deficient mice (FIG. 3D). These findings strongly demonstrate that Cnsk2 orchestrates the well-characterized diurnal oscillation of epithelial stem cell activity through repression of Nlrp6 activity.

Flavones are a class of flavonoids, which are a prominent constituent of the human diet. The dietary flavonoid apigenin is a promising drug for the treatment of several illnesses associated with circadian rhythm disruption. Apigenin-treated wild-type mice on LD cycles had less severe body-weight loss upon oral administration of dextran sodium sulfate (DSS) (FIG. 3F). Upon apigenin administration, a lower disease-activity index correlated with greater colon length as what was observed with other flavones (22). In agreement, a reduced infiltration of inflammatory cells was markedly evidenced on representative haematoxylin and eosin-stained sections of the colon from apigenin-treated mice when compared to controls (FIG. 3J). In contrast, no anti-inflammatory effect of apigenin was observed when mice were housed in darkness for three circadian cycles during DSS exposure.

We next determined whether apigenin may protect against DSS-induced colitis through Nlrp6. In line with our previous findings, treatment of mice lacking Nlrp6 with apigenin failed to improve wasting disease (FIG. 3I), did not alter colon length (FIG. 3J) and had no effect on inflammation in subsequent histological analysis (FIG. 3K). Collectively, these observations demonstrate that Nlrp6 determines to a large extent whether apigenin protects mice from intestinal inflammation.

By 16S rRNA gene sequencing, we next addressed whether the anti-inflammatory role of apigenin was associated with alterations in the bacterial composition of the gut microbiota. Statistical analysis of similarity (ANOSIM) on Jaccard distances revealed that the gut microbiota composition of apigenin-treated wild-type mice was markedly different from the one of controls ($R^2$=0.33, p=0.015; Fig. 4A).

Apigenin-induced changes among the bacterial OTUs included an expansion of several genera derived from Bacteroidetes, including *Alistipes, Parasatuerlla* and *Bacteroides*. More importantly, apigenin treatment in wild-type mice led to a reduction in *Clostridium* sensu stricto and unclassified *Ruminococcacceae* that were readily found to oscillate in Nlrp6-deficient mice. In line with previous findings (9), large-scale changes in the gut microbiota composition gave rise to a reduced bacterial diversity in the absence of Nlrp6 (p=0.001). Notably, the gut bacterial ecology of Nlrp6-deficient mice was characterized by a lowered abundance of non-flagellated and butyrate-producing bacteria belonging to the Bacteroidetes phylum (including *Alistipes, Barnesiella* and *Allobaculum*), which was correlated with an outgrowth of unclassified *Porphyromonadaceae* and *Clostridiales* genera. To ascertain the role of apigenin-induced dysbiosis on intestinal homeostasis further, vehicle- and apigenin-treated mice were co-housed over a three-week period before DSS challenge. Importantly, wasting disease was improved in co-housed vehicle-treated animals to a similar degree than what observed in wild-type mice receiving apigenin (FIG. 4B, C, D). In contrast, co-housing experiments in Nlrp6-deficient mice failed to reveal any differences in protection from colitis between co-housed and single-housed animals (FIG. 4E-G). Consistently, we failed to observe global changes in the composition of the gut microbiota (ANOSIM, p=0.283) from apigenin- and vehicle-treated Nlrp6-deficient mice (FIG. 4E, F, G). Together, these results show that entrainment of circadian clock by apigenin is accompanied by Nlrp6-dependent alterations in the gut microbiota, which are conferring a transmissible protection against intestinal inflammation.

Collectively, we conclude that Nlrp6 orchestrates the diurnal oscillation of IECs proliferation and of gut bacterial ecology. We demonstrated that Nlrp6 acts downstream of Csnk2, which can lengthen the circadian period in a variety of species (17, 18). More importantly, pharmacological inhibition of Csnk2 activity by dietary apigenin rendered mice protected against intestinal inflammation through Nlrp6. Apigenin is a naturally occurring plant flavone that is a biologically active ingredient of the traditional Chinese medicine to treat a wide range of diseases. Foremost, co-housing experiments revealed that the protective activity of apigenin-conditioned microbiota is even transmissible to adult wild-type mice. In contrast, apigenin-treated Nlrp6-deficient mice failed to confer protection to co-housed untreated mutant animals. Of note, the biological activity of apigenin mostly depends on the catabolic activity of some commensals with C-ring cleavage activity that are found within the gut microbiota (23). Further work is now eagerly awaited to evaluate the absorption and metabolism of flavones by the gut microbiota from IBD patients that is known to be less diversified. Understanding this paradigm is a prerequisite towards the development of personalized medicine in IBD patients who experienced severe metabolic and sleep disturbances. Further, recent genome-wide association studies have revealed an IBD-predisposing allele in the gene encoding CSNK2 (24) that is found to be less expressed in and translocated into the nucleus of colonic crypts from IBD patients (25, 26). Intriguingly, several other circadian clock components have also been found to be differentially expressed in IBD (25), while also being involved in IBD predisposition, including vitamin D receptor (rs11168249); nuclear factor and interleukin 3-regulated (rs4743820) (27, 28). Collectively, our results argue for the need to consider chronobiological therapy in IBD by improving the bioavailability of dietary flavones and nutraceuticals with known inhibiting activity on Csnk2, as it greatly influences the renewal of the intestinal epithelia and outcome of colitis by determining the architecture of the microbiota though Nlrp6.

REFERENCES

1. C. A. Lozupone, J. I. Stombaugh, J. I. Gordon, J. K. Jansson, R. Knight, Diversity, stability and resilience of the human gut microbiota. *Nature* 489, 220 (Sep. 13, 2012).
2. C. A. Thaiss et al., Transkingdom control of microbiota diurnal oscillations promotes metabolic homeostasis. *Cell* 159, 514 (Oct. 23, 2014).
3. W. W. Chang, Renewal of the epithelium in the descending colon of the mouse. 3. Diurnal variation in the proliferative activity of epithelial cells. *The American journal of anatomy* 131, 111 (May, 1971).
4. M. M. Hussain, X. Pan, Clock genes, intestinal transport and plasma lipid homeostasis. *Trends in endocrinology and metabolism: TEM* 20, 177 (May, 2009).
5. A. Mukherji, A. Kobiita, T. Ye, P. Chambon, Homeostasis in intestinal epithelium is orchestrated by the circadian clock and microbiota cues transduced by TLRs. *Cell* 153, 812 (May 9, 2013).
6. U. Schibler, P. Sassone-Corsi, A web of circadian pacemakers. *Cell* 111, 919 (Dec. 27, 2002).
7. T. Alterman, S. E. Luckhaupt, J. M. Dahlhamer, B. W. Ward, G. M. Calvert, Prevalence rates of work organization characteristics among workers in the U.S.: data from the 2010 National Health Interview Survey. *American journal of industrial medicine* 56, 647 (June, 2013).
8. S. Sahar, P. Sassone-Corsi, Metabolism and cancer: the circadian clock connection. *Nature reviews. Cancer* 9, 886 (December, 2009).
9. E. Elinav et al., NLRP6 inflammasome regulates colonic microbial ecology and risk for colitis. *Cell* 145, 745 (May 27, 2011).
10. S. Normand et al., Nod-like receptor pyrin domain-containing protein 6 (NLRP6) controls epithelial self-renewal and colorectal carcinogenesis upon injury. *Proceedings of the National Academy of Sciences of the United States of America* 108, 9601 (Jun. 7, 2011).
11. G. Y. Chen, M. Liu, F. Wang, J. Bertin, G. Nunez, A functional role for Nlrp6 in intestinal inflammation and tumorigenesis. *Journal of immunology* 186, 7187 (Jun. 15, 2011).
12. M. E. Hughes, J. B. Hogenesch, K. Kornacker, JTK_CYCLE: an efficient nonparametric algorithm for detecting rhythmic components in genome-scale data sets. *Journal of biological rhythms* 25, 372 (October, 2010).
13. J. Henao-Mejia et al., Inflammasome-mediated dysbiosis regulates progression of NAFLD and obesity. *Nature* 482, 179 (Feb. 9, 2012).
14. R. Nowarski et al., Epithelial IL-18 Equilibrium Controls Barrier Function in Colitis. *Cell* 163, 1444 (Dec. 3, 2015).

15. Y. Sun et al., Stress-Induced Corticotropin-Releasing Hormone-Mediated NLRP6 Inflammasome Inhibition and Transmissible Enteritis in Mice. *Gastroenterology* 144, 1478 (June, 2013).
16. M. Lefebvre et al., Peroxisome proliferator-activated receptor gamma is induced during differentiation of colon epithelium cells. *The Journal of endocrinology* 162, 331 (September, 1999).
17. E. E. Zhang et al., A genome-wide RNAi screen for modifiers of the circadian clock in human cells. *Cell* 139, 199 (Oct. 2, 2009).
18. B. Maier et al., A large-scale functional RNAi screen reveals a role for CK2 in the mammalian circadian clock. *Genes & development* 23, 708 (Mar. 15, 2009).
19. A. von Knethen, N. Tzieply, C. Jennewein, B. Brune, Casein-kinase-II-dependent phosphorylation of PPAR-gamma provokes CRM1-mediated shuttling of PPAR-gamma from the nucleus to the cytosol. *Journal of cell science* 123, 192 (Jan. 15, 2010).
20. D. Kelly et al., Commensal anaerobic gut bacteria attenuate inflammation by regulating nuclear-cytoplasmic shuttling of PPAR-gamma and RelA. *Nature immunology* 5, 104 (January 2004).
21. A. Plotnikov, D. Chuderland, Y. Karamansha, O. Livnah, R. Seger, Nuclear extracellular signal-regulated kinase 1 and 2 translocation is mediated by casein kinase 2 and accelerated by autophosphorylation. *Molecular and cellular biology* 31, 3515 (September, 2011).
22. E. K. Shin, H. S. Kwon, Y. H. Kim, H. K. Shin, J. K. Kim, Chrysin, a natural flavone, improves murine inflammatory bowel diseases. *Biochemical and biophysical research communications* 381, 502 (Apr. 17, 2009).
23. L. A. Griffiths, G. E. Smith, Metabolism of apigenin and related compounds in the rat. Metabolite formation in vivo and by the intestinal microflora in vitro. *Biochem J* 128, 901 (July, 1972).
24. A. Franke et al., Genome-wide meta-analysis increases to 71 the number of confirmed Crohn's disease susceptibility loci. *Nature genetics* 42, 1118 (December).
25. O. Palmieri et al., Systematic analysis of circadian genes using genome-wide cDNA microarrays in the inflammatory bowel disease transcriptome. *Chronobiology international* 32, 903 (August, 2015).
26. S. Koch et al., Protein kinase CK2 is a critical regulator of epithelial homeostasis in chronic intestinal inflammation. *Mucosal immunology* 6, 136 (January, 2013).
27. A. Franke et al., Genome-wide meta-analysis increases to 71 the number of confirmed Crohn's disease susceptibility loci. *Nature genetics* 42, 1118 (December, 2010).
28. L. Jostins et al., Host-microbe interactions have shaped the genetic architecture of inflammatory bowel disease. *Nature* 491, 119 (Nov. 1, 2012).

Throughout this application, various references describe the state of the art to which this invention pertains. The disclosures of these references are hereby incorporated by reference into the present disclosure.

The invention claimed is:

1. A method for treating dysbiosis associated with circadian clock disruption in a subject in need thereof, said method comprising steps of
   selecting a subject having dysbiosis associated with circadian clock disruption wherein said dysbiosis is characterized by a change and/or loss of diurnal variation of the gut microbiota, wherein said subject has an increased level of harmful gut bacteria and a reduced level of beneficial gut bacteria, and wherein the beneficial gut bacteria are selected from at least one of non-flagellated and butyrate-producing bacteria belonging to bacteroidetes phylum and the harmful gut bacteria are *Ruminococcus gnavus* or *Proteus mirabilis* bacteria; and
   administering to the subject an inhibitor of the casein kinase 2 (Csnk2) activity.

2. The method according to claim 1, wherein microbiome dysregulation includes dysbiosis and/or loss of diurnal rhythmicity of the gut microbiota.

3. The method according to claim 1, wherein the subject suffers from or is at risk of a circadian rhythm sleep disorder.

4. The method according to claim 1, wherein the inhibitor of the casein kinase 2 (Csnk2) activity is selected among flavones, tyrphostins and their derivatives.

5. The method according to claim 1, wherein the inhibitor of the casein kinase 2 (Csnk2) activity is selected from the group consisting in apigenin, luteolin, and tyrphostin AG99.

6. The method according to claim 1, wherein said non-flagellated and butyrate-producing bacteria belonging to bacteroidetes phylum are selected from *Alistipes, Banesiella* and *Allobaculum* bacteria.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic forward primer

<400> SEQUENCE: 1
actcctacgg gaggcagcag                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic reverse primer

<400> SEQUENCE: 2
ggactachvg ggtwtctaat                                               20
```